US006599529B1

(12) United States Patent
Skinhøj et al.

(10) Patent No.: US 6,599,529 B1
(45) Date of Patent: *Jul. 29, 2003

(54) MODIFIED RELEASE MULTIPLE-UNITS COMPOSITIONS OF NON-STEROID ANTI-INFLAMMATORY DRUG SUBSTANCES (NSAIDS)

(75) Inventors: Annette Skinhøj, Rødovre (DK); Poul Bertelsen, Vanlase (DK)

(73) Assignee: Nycomed Danmark A/S, Roskilde (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/508,594

(22) PCT Filed: Sep. 10, 1998

(86) PCT No.: PCT/DK98/00388

§ 371 (c)(1),
(2), (4) Date: Jul. 17, 2000

(87) PCT Pub. No.: WO99/12524

PCT Pub. Date: Mar. 18, 1999

(30) Foreign Application Priority Data

Sep. 11, 1997 (DK) .............................................. 1044/97

(51) Int. Cl.[7] .................................................. A61K 9/54
(52) U.S. Cl. ........................ 424/458; 424/451; 424/457; 424/464; 424/468; 424/469; 424/470; 424/472; 424/474; 424/484; 424/489

(58) Field of Search ................................. 424/464, 468, 424/469, 470, 474, 484, 451, 452, 458, 472, 489

(56) References Cited

U.S. PATENT DOCUMENTS

| 4,753,801 A | * | 6/1988 | Oren et al. | 424/465 |
| 4,842,867 A | * | 6/1989 | Ayer et al. | 424/473 |
| 5,043,167 A | | 8/1991 | Rotini et al. | 424/490 |
| 5,478,577 A | | 12/1995 | Sackler et al. | 424/489 |

FOREIGN PATENT DOCUMENTS

| EP | 0 438 249 A1 | 7/1991 |
| WO | WO 97/06787 | 2/1997 |
| WO | WO 97/32573 | 9/1997 |

* cited by examiner

Primary Examiner—James M. Spear
Assistant Examiner—Liliana Di Nola-Baron
(74) Attorney, Agent, or Firm—Peter F. Corless; Christine C. O'Day; Edwards & Angell, LLP

(57) ABSTRACT

An oral pharmaceutical modified release multiple-units composition for the administration of a therapeutically and/or prophylactically effective amount of a non-steroid anti-inflammatory drug substance to obtain both a relatively fast onset of the therapeutic effect and the maintenance of a therapeutically active plasma concentration for a relatively long period of time is disclosed.

51 Claims, 4 Drawing Sheets

MODIFIED RELEASE MULTIPLE-UNITS COMPOSITIONS OF NON-STEROID ANTI-INFLAMMATORY DRUG SUBSTANCES (NSAIDS)

This application is a 371 of PCT/DK98/00388 filed Sep. 10 1998,

The present invention relates to an oral pharmaceutical modified release multiple-units composition for the administration of a therapeutically and/or prophylactically effective amount of a non-steroid anti-inflammatory drug substance (in the following abbreviated "an NSAID substance") to obtain both a relatively fast or quick onset of the therapeutic effect and the maintenance of a therapeutically active plasma concentration for a relatively long period of time. The modified release multiple-units composition comprises at least two fractions of multiple units such as a first and a second fraction. The first fraction comprises individual units which are designed to quickly release the drug substance and the second fraction comprises individual units which are designed to slowly release the drug substance to enable a delayed and extended release of the drug substance. Typically, the second fraction comprises multiple units which are coated with a sustained release coating designed to release the drug substance in such a manner that the maintenance of a therapeutically active plasma concentration for a relatively long period of time are obtained. By suitable adjustment of the release pattern of the at least first and second fraction a composition is obtained which is adapted to once- or twice-a-day administration.

TECHNICAL BACKGROUND

Drug levels can be maintained above the lower level of the therapeutic plasma concentration for longer periods of time by giving larger doses of conventionally formulated dosage forms. However, it is not a suitable approach to increase dosage as such doses may produce toxic and undesired high drug levels. Alternatively, another approach is to administer a drug at certain intervals of time, resulting in oscillating drug levels, the so-called peak and valley effect. This approach is generally associated with several potential problems, such as a large peak (toxic effect) and valley (non-active drug level) effect, and a lack of patient compliance leading to drug therapy inefficiency or failure. If, however, the plasma concentration is kept constant over the therapeutic level using conventional tablets, an unacceptably high daily dosage is required if the active substance is not administered very frequently. Controlled release compositions are known which are designed to rapidly release a fraction of a total drug dose. This loading dose is an amount of a drug which will provide a desired pharmacological response as fast as possible according to the biopharmaceutical properties of the drug substance. Generally, such compositions in some more or less sophisticated manner are composed of a sustained release part and a part which either contains a free amount of the drug substance or it releases the drug substance in the same manner as if the drug substance had been formulated as a plain formulation (e.g. in the form of normal tablets or granulates). Such compositions which initially release a burst of a therapeutic agent and then release the agent at an essentially constant rate are described, e.g., in WO 95/14460 (Euroceltique S. A.) published on Jun. 1, 1995. The composition described therein relates to a sustained release opioid formulation comprising a plurality of substrates comprising the active ingredient in a sustained release matrix or coated with a sustained release coating comprising a retardant material. The sustained release beads are then coated with an opioid in immediate release form or, in the case the composition is in the form of a gelatine capsule, an amount of free opioid (i.e. the opioid is included as such and has not been processed into a specific formulation e.g. by means of pharmaceutically acceptable excipients) is incorporated into the gelatin capsule via inclusion of a sufficient amount of opioid within the capsule. In a further alternative, the gelatine capsule itself is coated with an immediate release layer of the opioid.

Generally, the rationale which lies behind the kind of compositions which have been described to enable an immediate release of a drug substance as well as a sustained release of the drug substance is to combine a traditional formulation approach (such as, e.g., i) plain tablets which have a disintegration time in water of at the most about 15 min for uncoated tablets, cf. Ph. Eur. (the requirements for coated tablets or capsules are at the most 30 min), ii) a traditionally formulated granulate or iii) loose powder of the drug substance itself) with a controlled release approach. By doing so the immediate release part of the composition is intended to release the drug substance in a manner which corresponds to a plain tablet formulation or the like and the term "immediate" is in such a context intended to denote that the release of the drug substance is faster than the release from a sustained release composition. The immediate release is in no way intended to be faster than that of a traditional or plain composition.

Especially in those cases where the drug substance has a low solubility in an acidic medium having a pH of from about 1 to about 3, i.e. a pH corresponding to the pH in the stomach, the traditional formulation approach will lead to a pharmaceutical composition which has a suitable fast disintegration time but not necessarily a suitable dissolution rate of the drug substance under acidic conditions, i.e. a plain tablet will rapidly disintegrate into granules but the dissolution of the drug substance from the composition and/or the disintegrated composition under acidic conditions may be unsuitable low due to the solubility properties of the drug substance itself. The availability of a drug substance with respect to absorption, i.e. entrance into the circulatory system, is dependant on the presence of the drug substance on dissolved form as it is generally accepted that only dissolved substances are capable of passing the mucous membranes in the gastro-intestinal tract. Therefore, it is important that the dissolution of the drug substance is suitably fast even under acidic conditions in order to enable an initial absorption already from the stomach so that a true fast or immediate therapeutic response is obtainable. Furthermore, if a drug substance—dependent on pH can exist on un-ionized as well as ionized form (e.g. acetyl salicylic acid which at an acid pH below its $pK_a$ value predominantly is present on an unloaded, i.e. un-ionized form, whereas at a pH above its $pK_a$ value predominantly is present on ionized form). For drug substances which are weak acids it is very important to ensure a proper bioavailability of the drug substance already under acidic conditions in order to achieve a true rapid therapeutic effect. However, the various approaches disclosed with respect to achievement of a combination of a rapid and a sustained effect (e.g. in the publications mentioned above) do not seem to take the above-mentioned factors into account and, hence, there is a need for developing compositions which enable a true rapid onset of the therapeutic effect as well as a sustained effect. To this end, we have especially focused on compositions comprising a drug substance suitable for use in situations where a rapid effect is needed but also in situations where an extended effect is desirable in order to develop compositions suitable for administration less frequent than compositions on the market today, more specifically to enable administration on a once or twice daily basis. Examples of suitable drug substances are, e.g., substances which have a pain relief effect. More specifically, interesting drug substances are those belonging to the class of drug substances normally denoted NSAIDs or NSAID substances.

In EP-A-0 438 249A1 (ELAN Corporation P.L.C.) is given another example of a composition which has been designed to release naproxen immediately and sustained. However, as shown in Example 18 herein, the so-called immediate release of naproxen does not take place under acidic conditions, i.e. conditions prevailing in the stomach. Accordingly, such a composition is not within the scope of the present application.

As will be apparent from the following the present inventors have developed a composition in multiple-units form for a quick release as well and an delayed and extended release.

Multiple-units formulation techniques according to the invention aim at a modified release of a drug substance in a predetermined pattern to control the peak plasma concentration without affecting the bioavailability, i.e. the extent of drug availability. The release of an NSAID substance from a composition according to the present invention is controlled in a very flexible manner as described below. Many advantages are obtained, e.g., the frequency of undesirable side effects may be reduced, and due to the control of the time it takes to obtain the peak plasma concentration and the prolongation of the time at the therapeutically active plasma concentration, the frequency of the administration may be reduced to a dosage taken only twice or once a day. This also serves to improve patient compliance. A further advantage of the modified release multiple-units dosage form is that high local concentrations of the active substance in the gastro-intestinal system are avoided, due to the units being distributed freely throughout the gastrointestinal tract, independent of gastric emptying.

Moreover, patients suffering from pain and/or inflammatory conditions and/or related conditions very often require high daily dosages of NSAID substances. If such high dosage of an NSAID substance should be given only once a day, the release from the dosage form must be safe, predictable and reliable. The composition should also be very storage stable because an immediate release due to accidental damaging of e.g. the coating or capsule of a high dosage form may result in undesired high plasma concentrations, so-called dose dumping, which could cause undesired side effects. Furthermore, from a technical point of view, the release rate and the release pattern of the active drug substance from the composition should not significantly change during the shelf-life of the composition. Even a minor change in the release rate and/or release pattern may have a significant impact on the in vivo performance of the composition.

By use of a coated multiple unit dosage form, the risk of dose dumping due to e.g. rupturing of a coating is reduced because the amount of active ingredient in each coated unit is negligible.

The compositions according to the present invention are intended to reduce or essentially eliminate problems identified with other kind of compositions intended for administration once daily. Thus, a major disadvantage of the once-a-day treatment in the art may be a low plasma concentration at the end of the dosing period and thereby the lack of therapeutic response. As the treatment of pain and/or inflammatory conditions and/or related conditions, is a balance of therapeutic effect on the one hand and the risk of side effects on the other hand, e.g. due to accumulation of drug, the dosage interval is generally calculated so that the drug concentration is substantially decreased at the time of intake of the next dosage. Accordingly, the patient will very often suffer from disease symptoms before the drug concentration subsequent to the next dosage has reached the therapeutic level. In addition, it should be noted that in the treatment of pain and/or inflammatory conditions and/or related conditions, relatively higher dosages, corresponding to a relatively higher peak concentration, are often needed in case the symptoms break through. Accordingly, a relatively higher initial plasma concentration of an NSAID substance may be necessary compared to the plasma concentration at steady state.

However, to the best of our knowledge no oral non-steroid anti-inflammatory modified release pharmaceutical composition has been disclosed which at the same time can be produced in an easy, cheap and reliable manner and which provides a suitable profile for release of active substance (under acidic, neutral and basic conditions) resulting in an extended period of action so that the inflammatory condition is both rapidly alleviated after administration and avoided for a period of about 12 to 24 hours.

Therefore, there is a need for developing a composition comprising a non-steroid anti-inflammatory drug substance permitting the administration of dosages only once or twice a day in a safe and reliable manner, and which is easy to produce, preferably involving conventional production methods and as few production steps as possible. It is also important that an NSAID composition for daily administration comprises the active ingredient in such a way that the composition has a reliable dissolution rate since a change in the dissolution pattern of the NSAID substance could be disadvantageous for the patient.

BRIEF DISCLOSURE OF THE INVENTION

The purpose of the present invention is to provide an oral modified release multiple-units composition for administration of a daily dosage of an NSAID substance in a dosage form which only requires administration at the most twice daily, preferably once daily, and which overcomes the drawbacks of hitherto suggested formulations of modified release compositions containing an NSAID substance in that the dosage form both provides a substantially fast release from a first fraction comprising multiple units and a delayed and extended release from a second fraction of multiple units of the NSAID substance whereby alleviation of symptoms is achieved shortly after administration and is maintained for at least 12 hours, preferably 24 hours after administration.

A further aspect of the invention is to provide a process for the preparation of a composition of an oral pharmaceutical modified release multiple-units composition containing an NSAID substance, and in addition, a method for treating patients with a composition according to the invention whereby the interval between each administration is increased to about 12–24 hours.

Accordingly, the present invention relates to an oral pharmaceutical modified release multiple-units composition in unit dosage form for administration of a therapeutically and/or prophylactically effective amount of a non-steroid anti-inflammatory drug substance (an NSAID substance), a unit dosage form comprising two NSAID-containing fractions, i) a first NSAID-containing fraction of multiple-units for quick release of the NSAID substance, and ii) a second NSAID-containing fraction of multiple-units for extended release of the NSAID substance, the first fraction which—when subjected to dissolution method II as defined herein employing 0.07 N HCl as dissolution medium—releases at least 50% w/w of the NSAID substance present in the fraction within the first 20 min of the test, the second fraction being in the form of coated delayed release multiple-units for extended release of the NSAID substance.

The present invention also relates to a composition for the administration of a therapeutically and/or prophylactically effective amount of an NSAID substance to obtain both a relatively fast onset of the therapeutic effect and the maintenance of a therapeutically active plasma concentration for a relatively long period of time, a unit dosage of the composition comprising at least two fractions as follows:

a first fraction of quick release multiple-units for relatively quick release in vivo of an NSAID substance to obtain a therapeutically and/or prophylactically active plasma concentration within a relatively short period of time, and a second fraction of coated modified release multiple-units for extended release in vivo of an NSAID substance to maintain a therapeutically and/or prophylactically active plasma concentration in order to enable dosing once or twice daily, the formulation of the first and the second fractions, with respect to release therefrom and with respect to the ratio between the first and the second fraction in the unit dosage, being adapted so as to obtain:

a relative fast in vitro release of the NSAID substance from the first fraction of quick release multiple-units, as measured by the dissolution method 11 as defined herein, an extended in vitro release of the NSAID substance from the second fraction of extended release multiple-units relative to the in vitro release of the first fraction of the NSAID substance, as measured by the dissolution method III as defined herein, the quick release and the extended in vitro release being adapted so that the first fraction is substantially released when the release from the second fraction is initiated corresponding to at least 50% w/w release of the NSAID substance contained in the first fraction at the time when at the most about 15% w/w such as, e.g., at the most about 10% w/w or at the most about 5% w/w of the NSAID substance contained in the second fraction is released as measured by the dissolution method III as defined herein.

It should be noted that the dissolution methods mentioned above and throughout the specification of course may be adjusted to specific drug substances and in some cases replaced with other dissolution methods. However, the requirements claimed herein should still be fulfilled.

The modified release multiple-units dosage forms of the present invention achieve and maintain therapeutic plasma concentrations for a prolonged period of time. In order to achieve the relatively fast absorption for the first fraction it requires that NSAID substances dissolve in the stomach (cf. the discussion above). Since the solubility of an NSAID substance such as, e.g., lornoxicam is <1 mg/100 ml in 0.1 N HCl (aqueous solution of 0.1 N hydrochloric acid) the present inventors have found that incorporation such an NSAID substance in free form or in the form of a traditional formulation does not give the desired quick release under acidic conditions to enable a fast onset of the therapeutic effect in vivo. However, and as it will be discussed in detail below, a quick release of an NSAID substance (which is a weak acid or has a very low solubility under acidic conditions) takes place under acidic conditions provided that the drug substance is presented in a formulation wherein specific means has been used in order to manipulate the release rate so that the release becomes much faster than from a traditional composition. Thus, in contrast to the prior art composition in which focus only has been on the extended release rate part of the compositions and on the possibility of changing the release from this part, the present inventors have found it necessary to adjust the release rate from both the fast and the slow release part of a composition when the NSAID substance either has a very low solubility in 0.1 N hydrochloric acid or has a $pK_a$ below about 5.5 such as, e.g., about 4–5. Thus, both the fast release fraction and the delayed release fraction must be manipulated with respect to release in order to achieve a suitable overall release rate.

The first fraction of the composition constitutes the quick releasing part of the composition whereas the second fraction of the composition constitutes the delayed and extended release part of the composition. In the first fraction, the release rate is primarily governed by the formulation of the fraction, i.e. the ingredients employed and the processing of the ingredients to obtain the first fraction (cf. Danish Patent Application filed on Sep. 10, 1998 in the name of Nycomed Danmark). In those cases, where a coating is present on the units of the first fraction, the coating may of course also contribute to the control of the release of the active drug substance from the first fraction. In the second fraction, the release rate is primarily governed by the constitution and thickness of a controlled release membrane which are applied on pellet cores (also denoted "pellets").

The delayed and extended fraction is based on the application of a release controlling membrane. The release is being controlled by the membrane which makes the formulation much more robust and easier to manipulate and manufacture. Ideally there is no release controlling effect from the uncoated units of the second fraction, i.e. the uncoated multiple-units of the second fraction do not significantly contribute to any control of the extended release of the active drug substance but the uncoated multiple-units merely release the active drug substance freely without any significant retardation.

The modified release multiple-units dosage forms of the present invention achieve and maintain therapeutic levels and, at the same time, reduces the risks for any side effect, which are believed to be associated with high blood levels of NSAID substances. Furthermore, the delayed or extended release properties of the coating applied on the second fraction of the multiple-units dosage forms of the present invention are unaffected by the pH in the gastro-intestinal tract.

The first fraction of the multiple-units dosage form of the invention may also be in the form of coated multiple-units provided that the release rate of such a fraction is so fast in the dissolution medium employed in dissolution method II described herein that at least 50% w/w of the total dose of the first fraction is released within the first 20 min.

When a coating is present on the multiple-units of the first fraction then it could advantageous be of the same kind as an outer coating on the multiple-units of the second fraction. The employment of the same kind of coating for each fraction may be performed with substantially identical procedures and materials and the production cost can be kept at a low level.

DETAILED DISCLOSURE OF THE INVENTION

Accordingly, the present invention relates to an oral pharmaceutical modified release multiple-units composition in unit dosage form for administration of a therapeutically and/or prophylactically effective amount of a non-steroid anti-inflammatory drug substance (an NSAID substance), a unit dosage form comprising two NSAID-containing fractions, i) a first NSAID-containing fraction of multiple-units for quick release of the NSAID substance, and ii) a second NSAID-containing fraction of multiple-units for extended release of the NSAID substance, the first fraction which—when subjected to dissolution method 11 as defined herein employing 0.07 N HCl as dissolution medium—releases at least 50% w/w of the NSAID substance present in the fraction within the first 20 min of the test, the second fraction being in the form of coated delayed release multiple units for extended release of the NSAID substance.

As discussed above it is very important to secure that the release pattern of the active drug substance contained in the composition is suitable for a composition for administration once or twice daily. The employment of at least two different fractions of multiple-units gives very flexible formulation parameters. Thus, it is possible to vary i) the percentage of the total dose of the NSAID substance contained in each fraction and ii) the weight ratio between the different fractions. The system (i.e. formulation concept) is therefore very suitable to not only one specific drug substance but can within certain limits be applied on a class or many classes of active drug substances once the target release profile has been determined. Of course, a change from one active drug substance to another active drug substance may give rise to certain adjustments of the constitution of the individual fractions to the specific substance. In the following is given a discussion of how to determine a target profile for an active drug substance and the release requirements generally applicable for the group of active drug substances belonging to the non-steroid anti-inflammatory drug substances.

Dissolution Requirements

As described in the following, a target release profile can be designed for any NSAID substance. In the following the target release profile for a selected NSAID substance is described, namely lornoxicam.

Based on the knowledge of the pharmacokinetics of lornoxicam and a study performed by us employing a plain tablet and a solution (Hitzenberger G, Radhofer-Welte S, Takacs F, Rosenow D.: Pharmacokinetics of lornoxicam in man, Postgrad. Med. J. 1990, 66, pp S22–S26), a target in vivo profile for a once daily product has been estimated (FIG. 1).

The presumptions made in estimating this target profile were:

i) a double peak and an effective concentration for 24 hours are desired from a therapeutic point of view (i.e. plasma lornoxicam concentrations at 24 hours should be similar to the plasma concentration obtained 8–12 hours after administration of half the dose in the form of a plain tablet), ii) that the first fraction of the composition should have an absorption rate similar to or faster than that of plain tablets iii) that the peak concentration should not be higher than the peak concentration observed after administration of half the dose in the form of a plain tablet, and iv) that the second peak should appear about 5–6 hours after dosing.

A person skilled in the art is capable of determining the actual values with respect to the above-mentioned provisions and based on such values perform any necessary correction to the estimated profile (target profile).

The estimated target plasma profile as well as the profile from plain tablets have been deconvoluted with plasma concentrations from an oral solution to give an estimated in vivo dissolution profile (FIG. 2). All data were normalised to a dose of 16 mg. In the deconvolution a time interval of 0.5 hours was employed (cf. Langenbucher F., and H. Möller: Correlation of in vitro drug release with in vivo response kinetics. Part I: Mathematical treatment of time functions. Pharm. Ind. 1983, 45, pp 623–8 and Langenbucher F. and H. Möller: Correlation of in vitro drug release with in vivo response kinetics. Part II: Use of function parameters. Pharm. Ind. 1983, 45, pp 629–33).

The presumptions in making this deconvolution were that the daily dose of lornoxicam is the same irrespective of whether a once daily composition or a plain tablet or a solution were administered, The estimated in vivo dissolution profile for a once daily product can be used as the target in vitro profile for the combination of a fast or quick release fraction (i.e. the first fraction) and an extended or slow release fraction (i.e. the second fraction, coated pellets). The estimated in vivo dissolution profile for the once daily composition can be used as the target in vitro profile, when performing the dissolution tests in vitro with 1 hour in 0.1 N HCl and then shift to phosphate buffer pH 7.3 or 7.4 (dissolution methods III or IV described herein). This knowledge has been utilized in order to arrive at the dissolution requirements described in the following.

The presumptions made in using the estimated in vivo profile as target for in vitro profile were:

i) that a plain tablet will remain in the stomach for about 1 hour before a passage into the intestine takes place (estimated from the difference in $T_{max}$ between the solution (0.5 hours) and the plain tablet (1.5 hour), ii) that the correlation between the in vitro dissolution and the in vivo dissolution is a 1:1 correlation, and iii) that lornoxicam is absorbed through the whole gastrointestinal tract (including colon) in order not to loose any amount of active drug substance ready for absorption into the circulatory system.

Before going into detail with respect to the release requirement to the first fraction, the second fraction and the composition in its final form, in the following is given details with respect to the target release profile for a once daily lornoxicam composition. The profile has been estimated as described above.

Taget release in vivo profile (corresponds to target release profile in vitro employing dissolution methods III or IV as described herein):

| Time (hours) | % w/w released lornoxicam |
| --- | --- |
| 0.5 | 21 (range: 10–25%) |
| 1 | 29 (range: 15–35%) |
| 2 | 37 (range: 25–45%) |
| 3 | 42 (range: 30–55%) |
| 4 | 52 (range: 40–65%) |
| 5 | 62 (range: 45–70%) |
| 6 | 69 (range: 50–75%) |

-continued

| Time (hours) | % w/w released lornoxicam |
| --- | --- |
| 7 | 75 (range: 55–80%) |
| 8 | 79 (range: 60–85%) |
| 9 | 83 (range: 60–90%) |
| 10 | 86 (range: 60–95%) |
| 12 | 89 (range: 65–99%) |
| 16 | 94 (range: at least about 85%) |
| 20 | 97 (range: at least about 90%) |
| 24 | 100 (range: at least about 90%) |

As apparent from the above, the first fraction must release the active drug substance quickly in 0.1 N HCl or in the dissolution medium employed in dissolution method II described herein, i.e. under conditions simulating the conditions in the stomach and under these conditions the second fraction does not release any significant amount of the active drug substance. In this connection it is important to note that even if the second fractions does not release any significant amount of the active substance within the first 20 min or 1 hours under acidic conditions, then the controlled release coating is not necessarily designed as an enteric coating, i.e. a coating which is insoluble at acidic pH and soluble at neutral/basic pH. The compositions according to the invention exemplified in the experimental section are examples on compositions wherein the controlled release coating of the second fractions is not an enteric coating. Furthermore, application of an enteric coating on e.g. pellets would not lead to an extended release of an active drug substance. The release will of course be delayed (no release under acidic conditions) but as the pH becomes neutral and alkaline, then the enteric coating dissolves, i.e. there is no membrane left to control the release.

Notably, the release of the active drug substance from the first fraction is at least 55% w/w such as, e.g., at least about 60% w/w, at least about 65% w/w, at least about 70% w/w, at least about 75% w/w or at least about 80% w/w of the total NSAID substance present in the first fraction within the first 20 min of the test, i.e. the dissolution method II (pH corresponding to 0.07 N HCl) as defined in the experimental section.

In one embodiment the composition may comprise modified release multiple units wherein the in vitro dissolution characteristics of the first fraction of quick release multiple-units within 0.5 hour provides a release as defined by the dissolution methods II as described herein of at least about 50% w/w, at least about 60% w/w, at least about 70% w/w, at least about 80% w/w, at least about 85% w/w, at least about 90% w/w or at least about 95% w/w calculated on the total amount of active drug substance contained in the first fraction.

In addition, the composition-may comprise modified release multiple units wherein the in vitro dissolution characteristics of the first fraction of quick release multiple units within 1 hour provides a release as defined by the dissolution methods II described herein of at least about 50% w/w, such as, e.g., at least about 60% w/w, at least about 70% w/w, at least about 80% w/w, at least about 85%, at least about 90% w/w or at least about 95% w/w calculated on the total amount of active drug substance in the first fraction.

As apparent from the discussion above, the overall release characteristics with respect to release of the active drug substance from the final composition are composed of the release characteristics of the first and the second fraction of multiple-units, respectively. With regard to compositions containing an NSAID substance intended for administration once or twice daily, the present inventors have found that the release characteristics of the second fractions most suitably should have the following order of magnitude provided that the release characteristics of the first fraction are as discussed above.

Accordingly, the in vitro dissolution characteristics of the second fraction of extended release multiple units may in one embodiment within 1 hour provide a release as defined by the dissolution method III described herein in the range of 0%–about 30% w/w, such as, e.g., in the range of 0%–about 20% w/w, in the range of 0%–about 10% w/w such as about 5% w/w calculated on the total amount of active drug substance in the second fraction.

Furthermore, the in vitro dissolution characteristics of the second fraction of extended release multiple units may within 3 hours provide a release as defined by the dissolution method III described herein in the range of about 10%–70% w/w, such as, e.g., in the range of about 10%–60% w/w, in the range of about 12%–50% w/w, in the range of 14%–45% w/w, in the range of about 15%–30% w/w, in the range of about 15%–20% w/w such as, e.g., about 17% w/w of the NSAID substance.

Within 6 hours, the in vitro dissolution characteristics of the second fraction of extended release multiple units may provide a release as defined by the dissolution method III described herein in the range of about 35%–95% w/w, such as, e.g., in the range of about 50%–90% w/w, in the range of about 50%–80% w/w, in the range of 50%–75% w/w, in the range of about 50%–60% w/w, in the range of about 53%–59% w/w such as, e.g. about 56% w/w of the NSAID substance.

In addition, within 9 hours the in vitro dissolution characteristics of the second fraction of extended release multiple units may provide a release as defined by the dissolution method III described herein in the range of about 50%–100% w/w, such as, e.g., in the range of about 60%–98% w/w, in the range of about 65%–95% w/w, in the range of about 70%–90% w/w, in the range of about 70%–80% w/w such as, e.g., about 76% w/w of the NSAID substance.

To ensure that the final composition has a proper constitution with respect to the weight amount of first fraction relative to the amount of second fraction, the in vitro dissolution characteristics of the first and second fractions are in one embodiment adapted so that the first fraction is substantially released when the release from the second fraction is initiated, corresponding to at least 50% w/w release of the first fraction at the time at the most about 15% w/w such as, e.g., at the most about 10% or at the most about 5% w/w of the second fraction is released, as measured by the dissolution method III described herein. In addition, the in vitro dissolution characteristics of the first and second fractions in the same or a second embodiment as mentioned above are adapted so that the first fraction is substantially released when the release from the second fraction is initiated, corresponding to at least 70% w/w release of the first fraction at the time at the most about 20% w/w such as, e.g., at the most 15% w/w or at the most about 10% wow of the second fraction is released, as measured by the dissolution method III described herein.

Apart from the requirements to the individual fractions contained in the composition it is of course of utmost importance to ensure that the composition in its final form has in vitro dissolution characteristics which give evidence for a suitable in vivo behaviour, i.e. a fast onset of the effect together with an extended release of the active drug substance to ensure a therapeutic and/or prophylactic effect upon administration once or twice daily.

The two fractions of multiple units may be selected, with respect to the release from each fraction and the ratio between the two fractions, so that the in vitro dissolution characteristics of the composition within 1 hour provide a release of the NSAID substance in the first and second fractions in the range of from about 5% w/w to about 50% w/w, such as, e.g., in the range of from about 5% w/w to about 45% w/w, in the range of from about 15% w/w to about 40% w/w, in the range of from about 20% w/w to about 35% w/w such as about 29% w/w, as defined by the dissolution method III described herein.

In addition, the two fractions of multiple units may be selected, with respect to the release from each fraction and the ratio between the two fractions, so that the in vitro dissolution characteristics of the composition within 3 hours provide a release as defined by the dissolution method III described herein in the range of from about 20% w/w to about 80% w/w, such as, e.g., in the range of from about 25% w/w to about 70% w/w, the range of from about 30% w/w to about 60% w/w, in the range of from 35% w/w to about 55% w/w such as about 42% w/w.

In an additional aspect, the two fractions of multiple units may be selected, with respect to the release from each fraction and the ratio between the two fractions, so that the in vitro dissolution characteristics of the composition within 6 hours provide a release as defined by the dissolution method III described herein in the range of from about 40% w/w to about 98% w/w, such as, e.g., in the range of from about 50% w/w to about 95% w/w, in the range of from about 60% w/w to about 90% w/w, in the range of from about 60% w/w to about 85% w/w, in the range of from about 60% to about 83% such as about 69–70% w/w.

Furthermore, the two fractions of multiple units may be selected, with respect to the release from each fraction and the ratio between the two fractions, so that the in vitro dissolution characteristics of the composition within 9 hours provide a release as defined by the dissolution method III described herein in the range of from about 50% w/w to about 100% w/w, such as, e.g., in the range of from about 60% w/w to about 99% w/w, in the range of from about 70% w/w to about 98% w/w, in the range of from about 70% w/w to about 97% w/w, in the range of from about 75% w/w to about 96% w/w, such as in the range of from about 80% w/w to about 96%, such as about 80–85% w/w.

In a preferred embodiment, the composition fulfils the above criteria with respect to the dissolution characteristics of the composition in the full time span mentioned.

The percentage of NSAID substance in the first fraction is in the range of about 5%–50% w/w such as, e.g., in the range of about 10%–45% w/w, in the range of about 15%–45% w/w, in the range of about 20%–40% w/w, in the range of about 25%–40% w/w, in the range of about 25%–35% w/w such as, e.g., about 30% w/w, calculated on the total amount of NSAID substance in the composition.

The percentage of NSAID substance in the second fraction is in the range of about 30%–99% w/w such as, e.g. in the range of about 40%–98% w/w, in the range of about 45%–95% w/w, in the range of about 50%–95% w/w, in the range of about 55%–85% w/w, in the range of about 60%–80% w/w, in the range of about 60%–75% w/w, in the range of abut 65%–75% w/w such as, e.g., about 70% w/w, calculated on the total amount of NSAID substance in the composition.

In a preferred embodiment, the multiple units of the second and, when appropriate, the first fraction are coated, cross-sectionally substantially homogeneous pellets.

It is preferred that the multiple units of the first fraction result in a peak plasma concentration of the NSAID substance which is substantially the same as the peak concentration resulting from the second fraction. As the peak plasma concentration of the second fraction is adapted so that plasma concentration has a prolonged character due to the dissolution characteristics of the fraction described herein, the peak of this second fraction should preferably substantially represent the upper level of the therapeutic plasma concentration. In a preferred embodiment, the plasma concentration level is of such a size that no NSAID substance is in excess.

Since the total amount of NSAID substance contained in the first fraction is balanced compared to the total amount of NSAID substance in the composition, a peak plasma concentration of NSAID substance derived from the first fraction which is higher than the peak concentration resulting from the second fraction does not necessarily represent a substantial waste of the NSAID substance.

However, unless the patient suffers from heavy breakthrough symptoms wherein a higher plasma concentration than the plasma concentration for maintaining symptom alleviation often seems to be needed, the concentrations obtained from the first fraction should not exceed the peak from the second fraction.

Even in the circumstances wherein the peak of the first fraction is preferably higher than the peak from the second fraction, unsuitable high plasma concentrations (within the toxic level) derived from the first fraction may easily be avoided by adjusting the amount of active drug substance contained in the first fraction.

In another embodiment, e.g. in the circumstances wherein the patient is well treated by administration once or twice a day with a composition according to the invention, the first fraction may be adapted so that it results in a peak plasma concentration of the NSAID substance which is lower than the peak concentration resulting from the second fraction. This would not necessarily result in breakthrough symptoms as the NSAID substance remaining in the plasma from the previous dosage administered may contribute to maintaining the plasma concentration sufficiently high until the second fraction of the composition is released. In other cases, the daily dosage may be administered at a suitable time of the day when the patient has experienced less need for the NSAID, e.g. before bedtime.

Accordingly, an important aspect of the invention is an embodiment wherein the first fraction results in a therapeutically active plasma concentration of the NSAID substance until the delayed release of an NSAID substance from the second fraction of modified release multiple units contributes to the maintenance of a therapeutically active plasma concentration of the NSAID substance.

As discussed above, the multiple-units of the first fraction may be in the form of uncoated pellet cores, coated pellet cores, granules, a granulate or small plain tablets provided that the requirements with respect to release of active drug substance in 0.1 N HCl and under conditions as those described under dissolution method II herein are fulfilled. In those cases, where the first fraction is in the form of coated pellets, the time lag of the release from the second fraction relative to the first fraction may be obtained by a modified release coating of the second fraction which is present in a range of about 2%–80% such as, e.g., about 2%–70%, about 2–60%, about 3–50%, about 3–40%, about 4–30%, about 5–20% or about 2–5%, relative to the uncoated unit.

It is also preferred that the modified release coating of the fraction(s) is substantially water-insoluble, but water-diffusible and substantially pH-independent which will facilitate an absorption independent of the presence of food in the stomach.

Dosage

In general, the dosage of the active drug substance present in a composition according to the invention depends inter alia on the specific drug substance, the age and condition of the patient and of the disease to be treated.

Compositions according to the invention intended for once daily administration will generally contain a daily dose of the active drug substance whereas compositions according to the invention intended for twice daily administrations will generally contain half the daily dose of the active drug substance. However, the daily dose may be divided into several dosage forms.

In the following is listed the recommended daily doses for selected NSAID substances.

Aceclofenac: 200 mg
Diclofenac: 100 mg
Etodolac: 400 mg
Fenbufen: 900 mg
Fenoprofen: 1.5
Flurbiprofen: 200 mg
Ibuprofen: 1.6 g
Indometacin: 100 mg
Ketoprofen: 200 mg
Meloxicam: 15 mg
Nabumeton: 1 g
Naproxen: 750 mg
Piroxicam: 20 mg
Sulindac: 300 mg
Tenoxicam: 20 mg
Tiaprofenic acid: 600 mg
Tolfenamic acid: 400 mg
Tolmetin: 800 mg The amount of an NSAID substance of the modified release multiple-units composition according to the invention may be selected so that is corresponds to about 1 mg, 2 mg, 3 mg, 4 mg, 5 mg, 8 mg, 10 mg, 12 mg, 16 mg, 20 mg, 24 mg, 25 mg, 30 mg, 3 mg, 50 mg, 60 mg, 100 mg, 200 mg, 300 mg, 400 mg, 500 mg, 600 mg, 700 mg, 800 mg, 900 mg, 1 g, 1.1 g, 1.2 g, 1.3 g or 1.6 g of NSAID substance which are dosages generally known in the art. However, the composition according to the invention preferably comprises an amount of an NSAID substance which is a daily therapeutically effective amount of the NSAID substance.

Generally, with conventional dosage forms such as plain tablets comprising an NSAID substance, it is not always possible to obtain identical release profiles when different dosages are administered together as the load of active ingredient may differ depending on the size of the tablet. The release profile for 100 mg given in a single dosage may thus differ from 100 mg given as 5 dosages comprising 20 mg each. Not even with the commercially available modified release dosage forms, a substantially identical release profile within the different dosages is always observed.

With a composition according to the present invention, it is now possible to administer different dosages with identical release profiles (cf. results reported in the experimental section). For example, if each modified release multiple-units composition according to the invention is prepared with the same type of multiple units of the first and second fractions and in the same ratios, each of the dosage forms may be administered together to obtain any desired total dosage without altering the overall release profile from the total dosage. Accordingly, reliable and predictable plasma concentrations during the complete time span between administration may be obtained independently of the total dosage.

Therefore, a further advantage of the composition according to the invention is that the composition may be produced in different series of dosage forms of e.g. 4 mg, 8 mg, 12 mg, 16 mg, 24 mg, 32 mg etc., each of the series having individual properties resulting from the design of modified release of the first and second fractions as well as from the ratio between the fractions. Any desired total dosage can then be selected from the relevant dosage forms within each of the series.

The preferred dosage form according to the invention is in the form of a capsule, tablet, sachet etc. The size of the dosage form is adapted to the amount of the NSAID substance of the composition.

The above suggested dosage amounts should not be regarded as a limitation of the scope of the invention as it is obvious for the skilled person that any desired amount of the NSAID substance may be applied and is only limited by the size of the composition and the type of the NSAID substance.

The overall goal of the present invention is to provide a composition in unit dosage form for the administration of a therapeutically effective amount of an NSAID substance once a day. However, as some patients may still need to, or prefer to, receive administration twice a day, the invention should not be limited to a once-a-day composition as long as each of the unit dosage forms fulfils the criteria with respect to the dissolution mentioned above.

In a further aspect, the invention relates to a process for the preparation of an oral pharmaceutical modified release composition, the process comprising incorporating into the unit dosage at least two fractions as follows:

a first fraction of quick release multiple-units for relatively quick release in vivo of an NSAID substance to obtain a therapeutically or prophylactically active plasma concentration within a relatively short period of time, and a second fraction of coated extended release multiple-units for extended release in vivo of an NSAID substance to maintain a therapeutically active plasma concentration in order to enable dosing once or twice daily, the formulation of the first and the second fractions, with respect to release therefrom and with respect to the ratio between the first and the second fraction in the unit dosage, being adapted so as to obtain:

a relative quick in vitro release of the NSAID substance from the first fraction of quick release multiple-units, as measured by the dissolution method II defined herein, an extended in vitro release of the NSAID substance from the second fraction of extended release multiple-units relative to the in vitro release of the first fraction of the NSAID substance, as measured by the dissolution method III as defined herein, the quick release and the extended in vitro release being adapted so that the first fraction is substantially released when the release from the second fraction is initiated corresponding to at least about 50% w/w release of the NSAID substance contained in the first fraction at the time when about 5% w/w of the NSAID substance contained in the second fraction is released as measured by the dissolution method III as defined herein.

Definitions of Selected Terms Used Herein

The term "modified release multiple-units composition" used in the present context is defined as the release of the drug differs from that of a traditional composition. The release rate is in other words controlled and it is possible to manipulate the release rate by means of e.g. changing the formulation parameters. The rate is often controlled in such a manner that the plasma concentration levels are maintained for the longest possible period above the therapeutic (the therapeutically active) level, but below the toxic level. However, the term "modified" is not restricted to an extended or prolonged effect, the term "modified" may as well cover the situation where the release rate is manipulated in such a manner that a quicker release than normally expected is obtained. Thus, in the present context the terms "quick", "fast" and "enhanced" release as well as "controlled", "delayed", "sustained", "prolonged", "extended" and other synonyms well known to a person skilled in the art are covered by the term "modified".

The term modified release in the present context refers to a composition which can be coated or uncoated and prepared by using pharmaceutically acceptable excipients and/or specific procedures which separately or together are designed to modify the rate or the place at which the active ingredient or ingredients are released (Ph. Eur. 97).

The term "extended release" in the present context refers to a modified release composition of which the release of the active ingredient and its subsequent absorption are prolonged in comparison with a conventional non-modified form (Commision of the European Communities).

The terms "quick release", "fast release" or "enhanced release" in the present context refer to a modified release composition of which the release of the active ingredient and its subsequent absorption are fast. More specifically, the terms "quick release", "fast release" or "enhanced release" mean that for a composition—when subjected to a dissolution method II described herein—at least about 50% w/w of the active substance is dissolved within the first 20 min of the test.

The term "fraction" of multiple units in the present context refers to a part of the multiple units of a dosage unit. One fraction will generally differ from another fraction of multiple units of the dosage unit. Even though only two fractions have been defined, it is within the scope of the invention to have more than two fractions in one dosage unit. Accordingly, the dosage unit according to the invention comprises at least two fractions.

The term "dosage unit" in the present context refers to one single unit, e.g. a capsule, tablet, a sachet or any other relevant dosage form known within the art. A dosage unit represents a plurality of individual units which in accordance with the general state of the art may be in the form of a capsule, a tablet, a sachet, etc.

The term "bioavailability" designates the rate and extent to which the drug is absorbed from the modified multiple-units composition.

In the present context the term "therapeutically active plasma concentration which enables dosing once or twice daily" includes the situation wherein the NSAID substance administered has been metabolised to active metabolites resulting in a therapeutic effect for the stated period. It also includes the situation wherein the NSAID substance administered is present in a periferal compartment resulting in a therapeutic effect for the stated period.

The terms "NSAIDs" or "NSAID substances" are used herein to designate a group of drugs that belongs to non-steroid anti-inflammatory drug substances and pharmaceutically acceptable salts, prodrugs and/or complexes thereof as well as mixtures thereof.

The therapeutic classes mentioned herein are in accordance with the ATC (Anatomical Therapeutic Chemical) classification system.

Active Drug Substances

In the following are given examples of active drug substances which may be incorporated in a composition according to the invention. A majority of the active drug substances mentioned are weak acids, i.e. substances which have a $pK_a$ value below about 5.5 such as, e.g., in a range of from about 3.0 to about 5.5 or in a range of from about 4.0 to about 5.0. In this connection it can be mentioned that the $pK_a$ value for lornoxicam is about 4.7, for naproxen about 4.2, for indometacin about 4.5 and for acetylsalicylic acid about 3.5. When such substances which have a $pK_a$ value of between about 3.0 to about 5.5 is employed in the composition, the present inventors have found that the first fraction should be in the form of uncoated multiple-units as the coating or the manufacture of the units to a form suitable for application of a coating seem to have a retarding effect on the release rate of the active drug substance from the first fraction (see the experimental section). Moreover, active drug substances like those mentioned above (i.e. weak acids having a $pK_a$ value of at the most about 5.5 or about 5.0) generally have a poor solubility in media having a pH below the $pK_a$ value; as an example the solubility of lornoxicam at a pH corresponding to 0.1 N HCl is less than about 1 mg/100 ml at room temperature and active drug substances like acetylsalicylic acid, indometacin and naproxen are regarded as substances which are practically insoluble in water and 0.1 N HCl at room temperature. From the discussion relating to solubility and availability of the active drug substance in order to get access to the circulatory system it is should be appreciated that the release (dissolution) of the active drug substance from the first fraction should be quick under acidic conditions, e.g., in 0.1 N HCl even if the active drug substance has a very low solubility in this medium. First fractions containing such active drug substances are generally not in the form of coated multiple-units in compositions according to the invention (cf. the discussion above).

However, when the active drug substance incorporated in a composition according to the invention has a $pK_a$ value of at least about 5.0 such as at least about 5.5 the multiple-units of the invention may as well be in the form of coated multiple-units such as, e.g., coated pellet cores.

The first fraction is normally uncoated when the NSAID substance has a solubility in 0.1 N hydrochloric acid at room temperature of at the most about 0.5% w/v such as, e.g. at the most about 0.1% w/v, at the most about 0.05% w/v, at the most about 0.03% w/v, at the most about 0.01% w/w, at the most about 0.007% w/v, at the most about 0.005% w/v, at the most about 0.003% w/v, at the most about 0.002% w/v or at the most about 0.001% w/v.

The first fraction may be coated when the NSAID substance has a solubility in 0.1 N hydrochloric acid at room temperature of at least about 0.1% w/v such as e.g. at least about 0.5% w/v or at least about 1% w/v.

Relevant examples of NSAID substances suitable for use in compositions according to the invention are:
aminoarylcarboxylic acid derivatives like e.g. enfenamic acid, flufenamic acid, isonixin, meclofenamic acid, mefenamic acid, morniflumate, niflumic acid, and tolfenamic acid,
arylacetic acid derivatives like e.g. aceclofenac, acemetacin, amfenac, bromfenac, cimmetacin, diclofenac, etodolac, fentiazac, glucametacin, indomethacin, lonazolac, metiavinic acid, oxametacine, pirazolac, proglumetacin, sulindac, tiaramide, tolmetin, and zomepirac, arylcarboxylic acids like e.g. ketorolac and tinoridine, arylpropionic acid derivatives like e.g. alminoprofen, bermoprofen, carprofen, dexibuprofen, fenbufen, fenoprofen, flunoxaprofen, flurbiprofen, ibuprofen, ibuproxam, ketoprofen, loxoprofen, naproxen, oxaprozin, pranoprofen, protizinic acid, and tiaprofenic acid, pyrazoles like e.g. epirizole, pyrazolones like e.g. benzpiperylon, mofebutazone, oxyphenbutazone, phenylbutazone, and ramifenazone, salicylic acid derivatives like e.g. acetaminosalol, acetylsalicylic acid, benorylate, eterisalate, fendosal, imidazole salicylate, lysine acetylsalicylate, morpholine salicylate, parsalmide, salamidacetic acid and salsalate, thiazinecarboxamides like a.o. ampiroxicam, droxicam, lornoxicam, meloxicam, piroxicam, and tenoxicam, others like bucillamine, bucolome, bumadizon, diferenpiramide, ditazol, emorfazone, nabumetone, nimesulide, proquazone and piroxicam (e.g. in the form of a betacyclodextrin complex).

From a market point especially the following NSAIDs are interesting: lornoxicam, diclofenac, nimesulide, ibuprofen, piroxicam, piroxicam (betacyclodextrin), naproxen, ketoprofen, tenoxicam, aceclofenac, indometacin, nabumetone, acemetacin, morniflumate, meloxicam, flurbiprofen, tiaprofenic acid, proglumetacin, mefenamic, acid, fenbufen, etodolac, tolfenamic acid, sulindac, phenylbutazone, fenoprofen, tolmetin, acetylsalicylic acid, dexibuprofen and pharmaceutically acceptable salts, complexes and/or prodrugs and mixtures thereof.

Other relevant active drug substances are COX-2 (COX is an abbreviation for cyclooxygenase) inhibitors like e.g. celecosib and flosulide.

At present, the most preferred drug substance is lornoxicam and pharmaceutic ally acceptable salts, complexes and prodrugs thereof. Lornoxicam may be present in a composition according to the invention as the sole drug substance or in combination with other drug substances.

The modified release oral dosage form of the present invention preferably includes an NSAID substance as the therapeutically active ingredient in an amount corresponding to from 1 to about 1600 mg of by weight. Alternatively, the dosage form may contain molar equivalent amount s of pharmaceutically acceptable salts thereof. The dosage form contains an appropriate amount to provide a substantially equivalent therapeutic effect.

A composition according to the invention may contain a further active drug substance. Relevant substances in this context are e.g. antidepressants, opioids, prostaglandine analogs (e.g. misoprostol), glucocorticosteroids, cytostatics (e.g. methotrexate), $H_2$ receptor antagonists (e.g. cimetidine, ranitidine), proton pump inhibitors (e.g. pantoprazole, omeprazole, lansoprazole), antacids, acetaminophen (paracetamol), penicillamine, sulfasalazine and/or auranorfin.

The term "antidepressant" used in the present context includes tricyclic antidepressants as well as other antidepressants and mixtures thereof. Pharmaceutically acceptable salts and/or complexes of antidepressant are also within the definition of antidepressant. Thus, the term "antidepressant" is used here to designate a group of drugs that have, to varying degrees, antidepressive properties and/or suitable properties with respect to alleviation or treatment of neurogenic pain and/or phantom pain. In the present context the term "antidepressant" encompasses drug substances mainly from the therapeutic class NO6 or from the following drug classification: Psychoanaleptics excluding antiobesity preparations; anti-depressants/thymoanaleptics including substances used in the treatment of endogenous and exogenous depression such as, e.g., imipramine, nortriptyline, amitriptyline, oxipramol and MAO-inhibiting substances; lithium; combinations of drugs with ataractics; psychostimulants including drugs which increase the psychic and physical performance and which have a fatigue depressing, stimulating effect such as, e.g., fentyllines, fencamfamine, methylphenidate, amphetamines; pyscholeptic-psychoanaleptic combinations; nootropics [which are a class of psychoactive drugs which are claimed to have a selective action on integrative functions of the CNS. Their action is alleged to be particularly associated with intellectual function, learning and memory. Nootropics include preparations containing substances such as piracetam, pyritinol, pyrisuccideanol maleate, meclofenoxate, cyprodenate and their combinations with other substances, excluding those products with a vasodilatory action (see the therapeutic class CO4A). Combinations with cardiac glycosides are classified in the therapeutic class CO1A.]; and neurotonics and other miscellaneous products including products which are not classified above such as single or combination products containing bisibutiamin, deanol and derivatives, GABA, GABOB, N-acetyl asparaginic acid glutaminic acid and salts, kavain, phospholipid, succinodinitrate.

The presently most interesting drug substances belong to the tricyclic antidepressants. Relevant examples of antidepressants are: tricyclic antidepressants such as, e.g. dibenzazepine derivatives like carpipramine, clomipramine, desipramine, imipramine, imipraminoxide, imipramine pamoate, lofepramine, metapramine, opipramol, quinupramine, trimipramine; dibenzocycloheptene derivatives like amitriptyline, amitriptyline and chlordiazepoxide, amitriptyline and medazepram, amitriptyline and pridinol, amitriptyline and perphenazine, amitriptylinoxide, butriptyline, cyclobenzaprine, demexiptiline, nortriptyline, nortriptyline and diazepam, nortriptyline and perphenazine, nortriptyline and fluphenazine, nortriptyline and flupentixol, noxiptilin, protriptyline; dibenzoxepine derivatives like doxepin; and other tricyclic anti-depressants like adinazolam, amoxapine, dibenzepin, dimetacrine, dosulepin, dosulepin and diazepam, dothiepin, fluacizine (fluoracyzine, toracizin), iprindole, maprotiline, melitracen, melitracene and flupentixol, pizotyline, propizepine, and tianeptine; other antidepressants like 5-hydroxytryptophan, ademetionine, amfebutamone, amfebutamone hydrochloride, aminoptine, aminoptine hydrochloride, amisulpride, fluoxetine hydrochloride, fluoxetine, hypericin, lithium carbonate, sertraline hydrochloride, sertraline, St John's wort dry extract, trimipramine maleate, citalopram, citalopram hydrobromide, clomipramine chloride, clomipramine hydrochloride, d-phenylalanine, demexiptiline, demexiptiline hydrochloride, dimethacrine tartrate, dothiepin, dothiepin hydrochloride, doxepin, fluphenazine hydrochloride, fluvoxamine, fluvoxamine hydrogen maleate, fluvoxamine maleate, ginkgo biloba, indalpine, isocarboxazide, johanniskrauttrockenestrakt, 1-tryptophan, lithium citrate, lithium sulfate, lofepramine, maprotiline, maprotiline hydrochloride, maprotiline mesilate, medifoxamine, metaprimine fumarate, mianserin, moclobemide, nitroxazepine hydrochloride, nomifensine, nomifensine maleate, nomifensin hydrogenmaleat, oxitriptan, paroxetine, paraoxetine hydrochloride, pheneizine, pheneizine sulfate, piracetam, pirlindole, pivagabine, prolintane hydrochloride, propizepine hydrochloride, protriptyline hydrochloride, quinupramine, remoxipride hydrochloride, rubidium chloride, setiptiline maleate, tianeptine sodium, trazodone hydrochloride, venlafaxine hydrochloride, maprotiline, toloxatone, tranylcypromine, trazodone, trazodone hydrochloride, viloxazine, viloxazine hydrochloride,zimelidine, zimelidine dihydrochloride.

At present, the most interesting drug substances for use in a composition according to the invention are amitriptyline and/or imipramine and pharmaceutically acceptable salts, complexes and prodrugs thereof. Amitriptyline and/or imipramine may be present in a composition according to the present invention either as the sole drug substance or in combination with other drug substances. Amitriptyline is a very interesting drug candidate with respect to preventing and/or treating neurogenic pains and phantom pains.

The term "opioid" is used here to designate a group of drugs that are, to varying degrees, opium- or morphine-like in their properties. The term includes natural and synthetic opioids as well as active metabolites such as morphine-6-glucuronide and morphine-3-glucuronide, and mixtures of opioids. Pharmaceutically acceptable salts and/or complexes of opioids are also within the definition of opioids.

Further relevant examples of opioids for use in compositions according to the invention include alfentanil, allylprodine, alphaprodine, anileridine, benzylmorphine, bezitramide, buprenorphine butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocondone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, myrophine, nalbuphine, narceine, nicormorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, salts thereof, mixtures of any of the foregoing, mixed $\mu$-agonists/antagonists, $\mu$- and/or $\kappa$-agonists, combinations of the above, and the like.

Within the scope of the invention is of course that more than one active drug substance may be present in a composition, e.g. more than one NSAID substance and/or drug substances within the same or different therapeutic classes. Specific relevant therapeutic classes are MO1A (NSAIDs), RO5D, NO2 (analgesics), N2A (opioids) and N2B (non-narcotic analgesics).

Dose

In one embodiment of the present invention, the first fraction of multiple units comprises an amount of an NSAID substance corresponding to from about 50% to about 5% (between 1/2 and 1/20) of the daily dosage. In patients which are satisfactorily treated on 2–3 daily dosages of a conventional non-sustained formulation, the first fraction may in one example contain an amount of the NSAID substance corresponding to 40% of the daily dosage. The second fraction may then contain the remaining 60% of the daily dosage.

However, a preferred amount of the first fraction may comprise 30% of the daily dosage and the second fraction 70% of the daily dosage.

In another embodiment of the present invention, the first fraction of multiple units comprises an amount of an NSAID substance corresponding to the amount of the NSAID substance necessary for obtaining a therapeutic effect upon a first single oral dose of a conventional non-sustained formulation of the NSAID substance.

Formulation Details

First Fraction

As described above, the formulation of the first fraction depends on the specific active drug substance to be incorporated. If the solubility at room temperature in 0.1 N HCl is low and the $pK_a$ value is below about 5.5. or 5.0, then the first fraction is in the form of uncoated multiple-units. A very suitable formulation of the first fraction has under such conditions been found to be in the form of a granulate wherein special means have been employed in order to ensure a quick release of the poor soluble active drug substance. The granulate is typically prepared by wet-granulation (a process well known for a person skilled in the art) employing as little organic solvent as possible in order to reduce any environmental and personal risk. Furthermore, the present inventors have found that incorporation of an antacid-like substance like, e.g., sodium bicarbonate (sodium hydrogencarbonate), magnesium carbonate, magnesium hydroxide, magnesium metasilicate aluminate and other alkaline substance, has a pronounced increasing effect on the release rate.

In one embodiment, the individual units of the relatively fast release fraction according to the invention will normally be a granulate having a size (average diameter) of at the most about 250 $\mu$m such as, e.g. at the most about 240 $\mu$m, at the most about 230 $\mu$m, at the most about 220 $\mu$m, at the most abut 210 $\mu$m, at the most about 200 $\mu$m, at the most about 190 $\mu$m, at the most about 180 $\mu$m, at the most about 175 $\mu$m, at the most about 150 $\mu$m, at the most about 125 $\mu$m, at the most about 100 $\mu$m, at the most about 90 $\mu$m or at the most about 80 $\mu$m.

As described above, the first fraction may also be in the form of coated multiple-units such as coated pellets provided that the $pK$, of the active drug substance is at least about 5.0 or 5.5. From the experimental section inter alia it appears that such coated cores may have the same coating as the coating of the second fraction, but the thickness of the coating differs in such a manner that the coating of the first fraction is much thinner than that of the second fraction. For further details with respect to coating see below.

Second Fraction

The individual units of the extended release fraction according to the invention will normally be pellets or beads having a size (average diameter) of from about 0.1 to 2 mm. The most preferred pellet size is from 0.5 to 0.8 mm. The pellets or beads comprise a combination of active substance, the NSAID substance and excipients.

When the pellets or beads are not coated, the combination of the active substance and the excipients is referred to as a core.

In the present context, the term "cores which are cross-sectionally substantially homogeneous" designates cores in which the active substance is not confined to an exterior layer on the core body, in other words normally cores which, through the cross-section of the core body, contain substantially the same type of composition comprising minor particles containing active substance, in contrast to the non-pareil type of cores which each consists of an excipient body with active substance applied to its surface. From this definition, it will be understood that the cores which are cross-sectionally substantially homogeneous will normally consist of a mixture of active substance with excipient(s), this mixture will not necessarily be qualitatively or quantitatively homogeneous through the total cross-sectional area of the core but may show, e.g., a concentration gradient of the NSAID substance or they may consist substantially solely of NSAID substance. In the following specification and claims, such cores which are cross-sectionally substantially homogeneous will, for the sake of brevity, often simply be designated "cores".

It is contemplated that the core comprising the NSAID substance in a substantially homogeneous form provides a more reproducible release of the active ingredient than compared to e.g. particles in which the active ingredient forms part of the coating.

It should, however, be understood that the invention is not limited to pellet formulation containing the above-mentioned cores; in principle, the type of cores can be any kind such as, e.g. matrices, non-pareil cores as well.

It is preferred that the release profile of the core of the individual unit is substantially non-limiting with respect to the desired release of the coated pellet, e.g. that the core itself provides at least about 90% w/w such as, e.g., at least about 95% w/w, at least about 97% w/w, at least about 98% such as about 100% release within 1 hour, measured in the in vitro dissolution test described in the Examples. However, pellet cores showing a slower release of the active substance are still within the scope of the invention.

Dosage Forms

The oral pharmaceutical modified release multiple-units formulation according to the invention will typically be a capsule containing a multiplicity of the units, typically more than 100, a sachet containing a multiplicity of the units, typically more than 1000, or a tablet made from a multiplicity of the units, typically more than 100, in such a manner that the tablet will disintegrate substantially immediately upon ingestion in the stomach into a multiplicity of individual units which are distributed freely throughout the gastrointestinal tract.

In the present context the term "once daily"/"once-a-day" is intended to mean that it is only necessary to administer the pharmaceutical formulation once a day in order to obtain a suitable therapeutic and/or prophylactic response; however, any administration may comprise co-administration of more than one dosage unit, such as, e.g., 2–4 dosage units if the amount of active substance required may not be formulated in only one composition unit or if a composition unit of a minor size is preferred.

In agreement with the above-mentioned definition of "once daily"/"once-a-day", "twice daily"/"twice-a-day" is supposed to mean that it is only necessary to administer the pharmaceutical formulation at the most twice a day in order to obtain a suitable therapeutic and/or prophylactic response in the patient.

Irrespective of the above-mentioned definitions of "once" and "twice" daily, a dosage unit constructed to deliver the active ingredient after only one daily administration is preferred. However, due to individual circumstances some patients may need a new dosage after e.g. 12 or 18 hours if the patient e.g. has an abnormal absorption or bowel transit time. If the individual has a relatively fast bowel transit time, some of the active ingredient may be excreted before the full dosage is released, or may be released in the colon from which the absorption may be decreased.

A multiple unit pharmaceutical composition according to the present invention is preferably formed as a unit dosage form which upon oral administration disintegrates into a multiplicity of individual units. The dosage unit form is preferably a solid dosage unit form such as, e.g., a tablet, a capsule, or a sachet, especially in the form of capsules.

The actual load of the NSAID substance in a pharmaceutical composition according to the invention, i.e. the concentration in % w/w of the NSAID substance calculated on the total weight of the multiple units, may depend on the particular NSAID substance employed in the formulation. The formulation principle employed in the present invention is very flexible. As an example it can be mentioned that compositions can be designed so that the load of the NSAID substance in the individual multiple units of the two fractions and the content of the two fractions for one dosage unit comprising e.g. 10 mg of NSAID substance is identical with another dosage unit comprising e.g. 100 mg, the release profile for each of the dosages will be identical. Consequently, an individual total dosage can be administered to the patient by combining the relevant dosage units e.g. selected from a series of 4, 8, 12, 16, 24 and 32 mg of the NSAID substance without altering the overall release profile of the total amount of the NSAID substance administered.

The compositions mentioned above may be prepared by conventional methods known in the art. The invention also relates to a method for preparing an oral pharmaceutical modified release multiple-units composition.

Coating

In a further embodiment, the invention relates to a method for preparing an oral pharmaceutical modified release multiple-units formulation in which a) individual units containing an active substance are coated with an inner film-coating mixture ("the inner coat") comprising a film-forming substance, b) the thus coated units are optionally provided with a first outer film layer comprising e.g. a stabilizing agent ("the middle coat"), c) the thus coated units of the second fraction are optionally provided with a second outer film layer comprising a film-forming agent ("the outer coat"), d) a mixture of individual units of the first and second fraction are formulated in a dosage form in the desired ratio of the two fractions.

In general, the inner coating is applied in an amount corrsponding to 2–20% w/w. The middle coating, if present, is applied in an amount corresponding to about 4% w/w of the uncoated units and the outer coat is applied in an amount corresponding to about 1–2% w/w of the uncoated units.

The film-forming agent of step c) may be so selected that adhesion between the units is prevented at elevated temperatures, the coated units are then subsequently heated to a temperature above 40° C., preferably not above 65–75° C., and thereby a continuous phase is formed in the inner film layer in homogeneous admixture with the film-forming substance. In some cases, this curing process may also take place before the outer coating layer may be applied.

The modified release coating is applied on the multiple units from a solution and/or suspension preferably in an aqueous solvent, but an organic coating composition may also be applied.

Examples of film-forming agents which are suitable for use in accordance with the present invention are agents selected from the group consisting of cellulose derivatives such as, e.g., ethylcellulose, cellulose acetate, cellulose propionate, cellulose butyrate, cellulose valerate, cellulose acetate propionate; acrylic polymers such as, e.g., polymethyl methacrylate; vinyl polymers such as, e.g., polyvinyl acetate, polyvinyl formal, polyvinyl butyryl, vinyl chloride-vinyl acetate copolymer, ethylene-vinyl acetate copolymer, vinyl chloride-propylene-vinyl acetate copolymer; silicon polymers such as, e.g., ladder polymer of sesquiphenyl siloxane, and colloidal silica; polycarbonate; polystyrene; polyester; coumarone-indene polymer; polybutadiene; and other high molecular synthetic polymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquer used in the form of an aqueous dispersion, such as that which is commercially available from Rohm Pharma under the tradename Eudragit®. In further preferred embodiments, the acrylic coating comprises a mixture of two acrylic resin lacquers commercially available from Rohm Pharma under the tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. Eudragit® RL/RS mixtures are insoluble in water and in digestive fluids. However, coatings formed from the same are swellable and permeable in aqueous solutions and digestive fluids. The Eudragit® RL/RS dispersions may be mixed together in any desired ratio in order to ultimately obtain a modified release formulation having a desirable dissolution profile. The most desirable modified release formulations may be obtained from a retardant coating based on Eudragit® NE 30 D, which is a neutral resin having a molecular weight of 800,000.

The amount of coating applied is adapted so as to obtain a predetermined dissolution characteristic of the fraction of the composition. The percentage by weight of the modified release coating on the individual pellet will, for the fraction providing the extended duration of effect of the NSAID substance, be at the most about 20% w/w on an average, such as, e.g. about 15% w/w, about 12% w/w, preferably at the most about 10% w/w on an average, more preferred in the range of about 3% to 6% w/w on an average, based on the weight of the uncoated individual pellet. The amount of coating applied depends on the predetermined dissolution characteristics of the particular core composition and the desired release profile of the fraction.

However, the amount of coating applied should also be adapted so that there will be no rupturing problems.

The coating may be admixed with various excipients such as plasticizers, anti-adhesives such as, e.g., colloidal silicium dioxide, inert fillers, and pigments in a manner known per se.

Tackiness of the water-dispersible film-forming substances may be overcome by simply incorporating an anti-adhesive in the coating. The anti-adhesive is preferably a finely divided, substantially insoluble, pharmaceutically acceptable non-wetting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially water-insoluble calcium sulphates, colloidal silica, titanium dioxide, barium sulphates, hydrogenated aluminium silicates, hydrous aluminium potassium silicates and talc. The preferred anti-adhesive is talc. The anti-adhesive or mixture of anti-adhesives is preferably incorporated in the coating in an amount of about 0.1–70% by weight, in particular about 1–60% by weight, and preferably about 8–50% by weight of the inner film layer. By selecting a small particle size of the talc, a larger surface area is obtained; the consequent higher anti-adhesive effect makes it possible to incorporate smaller amounts of specific anti-adhesives.

The individual modified release coated multiple-units may further comprise a middle coating between the "inner coat" and the "outer coat". Such coating may be adapted to stabilize the controlled release coated multiple-units and to prevent undesired changes of the release profile of each coated unit. Accordingly, the middle lacquer or coating may contribute to stability of the release profile of the dosage unit. Accordingly, the multiple units may further comprise an outer film layer.

In one aspect, the outer second layer comprises a water-based film-forming agent which prevents adhesion between the units at elevated temperatures and imparts flowability to the units, the water-based film-forming agent being anti-adhesive at temperatures above about 40° C., especially temperatures above about 50° C., such as a temperature between about 60° C. and about 120° C., and being selected from diffusion coating materials such as ethylcellulose or enteric coating materials such as anionic poly(meth)acrylic acid esters, hydroxypropylmethylcellulosephthalate, celluloseacetatephthalate, polyvinylacetatephthalate, polyvinylacetate phthalate-crotonic acid copolymerisates, or mixtures thereof, or water-soluble coating materials such as water-soluble cellulose derivatives, e.g. hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose or hydroxypropylmethylcellulose.

Examples of plasticizers for use in accordance with the present invention include triacetin, acetylated monoglyceride, rape oil, olive oil, sesame oil, acetyl tributyl citrate, acetyl triethyl citrate, glycerin, sorbitol, diethyloxalate, diethylmalate, diethylmaleate, diethylfumarate, diethylsuccinate, diethylmalonate, dioctylphthalate, dibutylsebacetate, triethylcitrate, tributylcitrate, glyceroltributyrate, polyethyleneglycol, propyleneglycol, 1,2-propyleneglycol, dibutylsebacate, diethylsebacate and mixtures thereof. The plasticizer is normally incorporated in an amount of less than 10% by weight, calculated on the dry matter content of the coating composition.

Pharmaceutically Acceptable Excipients

Apart from the active drug substance in the multiple units, the pharmaceutical composition according to the invention may further comprise pharmaceutically acceptable excipients.

In the present context, the term "pharmaceutically acceptable excipient" is intended to denote any material which is inert in the sense that it substantially does not have any therapeutic and/or prophylactic effect per se. A pharmaceutically acceptable excipient may be added to the active drug substance with the purpose of making it possible to obtain a pharmaceutical formulation which has acceptable technical properties. Although a pharmaceutically acceptable excipient may have some influence on the release of the active drug substance, materials useful for obtaining modified release are not included in this definition.

Filler/diluents/binders may be incorporated such as sucrose, sorbitol, mannitol, lactose (e.g., spray-dried lactose, α-lactose, β-lactose, Tablettose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium phosphate (e.g. basic calcium phosphate, calcium hydrogen phosphate), calcium sulfate, calcium carbonate. In pharmaceutical formulations according to the present invention, especially microcrystalline cellulose, L-hydroxypropylcellulose, dextrins, maltodextrins, starches and modified starches have proved to be well suited.

Disintegrants may be used such as cellulose derivatives, including microcrystalline cellulose, low-substituted hydroxypropyl cellulose (e.g. LH 22, LH 21, LH 20, LH 32, LH 31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®).

Surfactants may be employed such as nonionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan tri oleate, glyceryl monooleate and polyvinylalkohol), anionic (e.g., docusate sodium and sodium lauryl sulphate) and cationic (e.g, benzalkonium chloride, benzethonium chloride and cetrimide) or mixtures thereof.

Other appropriate pharmaceutically acceptable excipients may include colorants, flavouring agents, and buffering agents.

In the following examples, the invention is further disclosed.

MATERIALS AND METHODS

Figure 1:
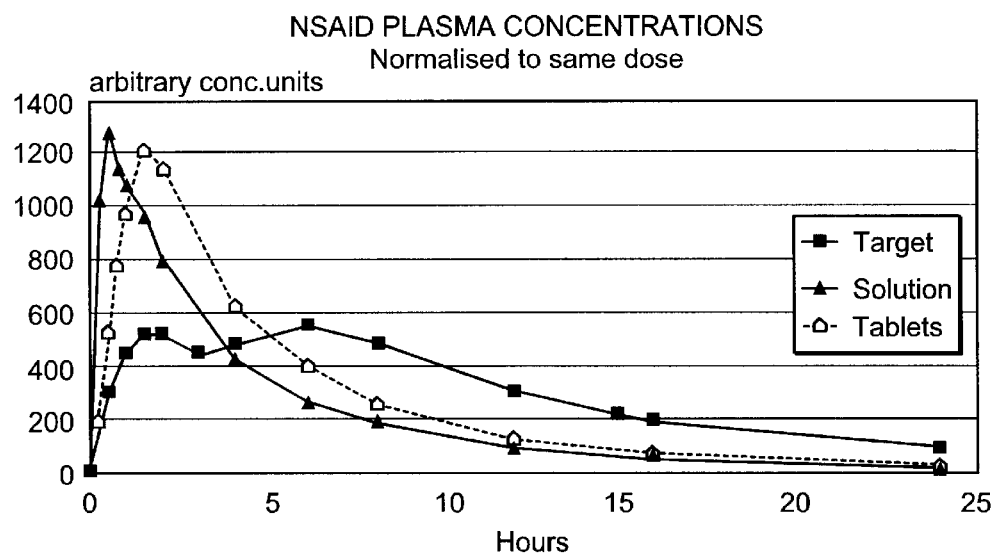
FIG. 1 shows a target plasma profile for lornoxicam together with a profile for plain tablets an solutions used to estimate the target profile.
Figure 2:
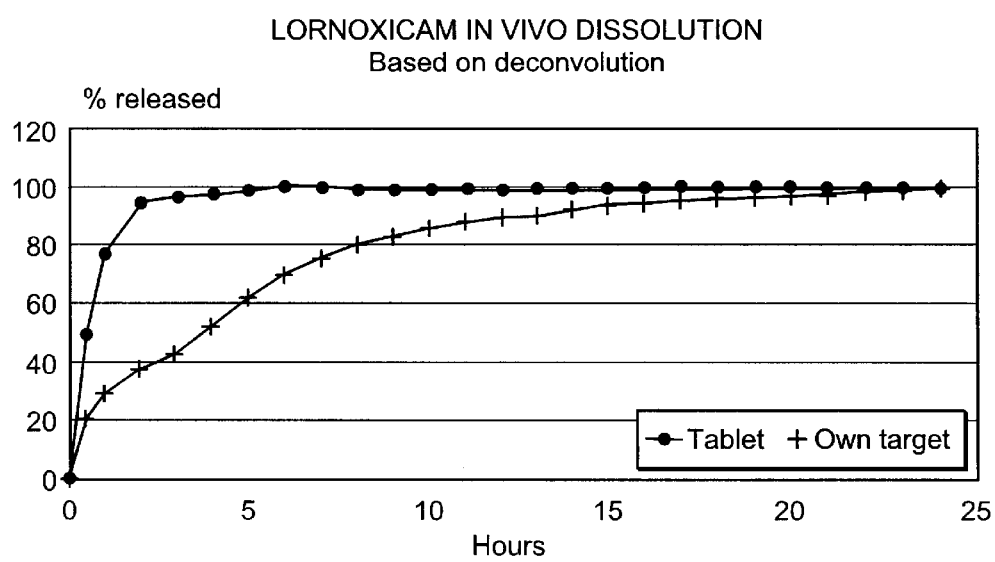
FIG. 2 shows target in vivo dissolution profile for lornoxicam once daily and plain tables.

Materials employed in the compositions which were investigated in the course of development of the present invention were as given in the following. In those cases where reference is given to an official pharmacopoeia, the reference is to the current edition of the stated pharmacopoeia.

The Following Abbreviations are Used:
  Ph. Eur.: European Pharmacopoeia
  USP/NF: United States Pharmacopoeia National Formulary
  DLS: Dansk Laegemiddelstandard

| Materials | Quality | Manufacturer |
| --- | --- | --- |
| Cellulosum microcristallinum (Avicel PH 101) | Ph.Eur. | FMC |
| Polysorbate 20 | Ph.Eur. | Henkel |
| Lactose monohydrate | Ph.Eur. | DMV |
| Carmellose sodium (Blanose 7 LFD) | Ph.Eur. | Aqualon |
| Maltodextrin (Glucidex 2) | USPNF | Roquette |
| Pregelatinised Starch (Starch 1500) | USPNF | Colorcon |
| Hypromellose (Methocel E 5 Premium) | Ph.Eur. | Dow |
| *Magnesii stearas* | Ph.Eur. | Akcros Chemicals |
| Talcum | Ph.Eur. | Whittaker, Clark and Daniels |
| Eudragit NE 30 D | Ph.Eur. | Rohm Pharma GmbH |
| Croscarmellose sodium (Ac-Di-Sol) | Ph.Eur. | FMC |
| Dibasic Calcium Phosphate, Anhydrous (Calcium hydrogen phosphate, mean particle size approx. 30 µm) | USPNF | Kyowa |
| Sodium bicarbonate (sodium hydrogencarbonate, mean particle size approx. 120 µm) | USPNF | Kirsch |
| Hydroxypropylcellulose (HPC L fine) | Ph.Eur. | Nippon Soda |
| Low-substituted Hydroxy Propyl Cellulose (LH21) | USPNF | Shin-Etsu |
| Ethanol, 96% | DLS | Danisco |
| Aqua Purificata | Ph.Eur. | |
| Naproxen | Ph.Eur. | Syntex Pharm. |
| Polyvidone 30 | Ph.Eur. | BASF |
| Isopropanol | Ph.Eur. | Sveda Kemi |

Whenever relevant, the mean particle size was determined by employment of a Malvern laser particle size analyser.

In the following five different dissolution methods I–V are described. In the table below is given an overview of the important differences between the five methods:

| | | Dissolution medium |
| --- | --- | --- |
| Dissolution method | pH | volume |
| I | 7.4 | 900 ml |
| II | 0.07 N HCl | 900 ml |
| III | 0.1 N HCl/7.3[a] | 750 ml of medium 1 and 250 ml of medium 2 |
| IV | 0.1 N HCl/7.4[b] | 750 ml of medium 1; after 1 hour this medium is changed to 900 m of medium 2 |
| V | 7.3 | 1000 ml |

[a] 750 ml 0.1 N HCl is employed in the first 1 hour of the test and then 250 ml of a medium 2 is added leading to a resulting pH of the dissolution medium of 7.3
[b] 750 ml 0.1 N HCl is employed in the first 1 hour of the test and is then replaced by 900 ml of a medium 2 having a pH of 7.4

The various dissolution methods have been employed to show that the method chosen for determining the dissolution profile of various compositions has an influence on the result obtained, i.e. different dissolution profiles are obtained when employing different dissolution methods.

The dissolution methods given below give details partly with respect to the test method and partly with respect to the analysis method. The following methods are directed to compositions containing lornoxicam as an example of an NSAID substance; however, in the case of compositions containing other drug substances than lornoxicam the test methods and details with respect to procedure and preparation of reagents are the same apart from an adjustment of the analysis method and the drug substance included in the standard solutions to conditions which are suitable for the drug substance in question. A person skilled in the art will have no difficulties in selecting a suitable method of analysis for a specific drug substance.

DISSOLUTION METHOD I pH 7.4 (lornoxicam)
Test Method
Apparatus: Ph. Eur. Dissolution test for solid dosage forms and USP XXIII <711> apparatus 2, equipped with Sotax AT7 and Perkin Elmer UV/VIS Spectrometer Lambda 2. The measurement was performed continuously using Perkin-Elmer Dissolution Software for Lambda Series UV/VIS Spectrometers Version 3.0/JAN 94. The calculations were performed using the same software.

Glass fibre filter: Whatman GF/F
Dissolution medium: 900.0 ml dissolution medium pH 7.4
Number of revolutions: 50 rpm
Stirrer: Paddle
Temperature of dissolution medium: 37° C.±0.5° C.
Measuring times: Every 5 minutes after the start of the test (details appear from the following examples)
Analysis Method
Detection wavelength: $\lambda$=378 nm
Measuring equipment: UV/VIS—spectrophotometer, 1 cm cuvette Preraration of Reagents Dissolution medium: An aqueous solution containing 10.1 mg/ml of sodium hydrogenphosphate dihydrate ($Na_2HPO_4$ $2H_2O$) and 1.6 mg/ml and sodium dihydrogenphosphate monohydrate ($NaH_2PO_4$ $H_2O$); the pH of the dissolution medium is 7.4.
Standards
Stock solutions: 2 stock solutions ($S_1$ and $S_2$) with a concentration of 200 µg/ml lornoxicam are prepared. Lornoxicam is dissolved in solvent for standards given below.
Standards: 20.00 ml of each of the stock solutions are added to the reference vessel (cf. below).
Solvent for standards:1.5% w/w aqueous sodium acetate solution:methanol (1:1 v/v)
Test Procedure
900 ml of the dissolution medium are filled to each of the vessels (typically three or six vessels for the product and one vessel for reference solution). The medium is heated to 37° C.±0.5° C. The product to be tested (e.g. a granulate, pellets, a final composition) is placed in the vessels, and the spindel is started. In the last vessel, 20.0 ml of each of the stock solutions are added. The absorbance of the samples and standards is measured at 378 nm with a zero setting towards the dissolution medium.

The percentage dissolved is measured over a suitable time interval.

DISSOLUTION METHOD II 0.07 HCl (lornoxicam)
Lornoxicam has a very low solubility in 0.1 N HCl inter alia in order to show that the relatively fast release fraction indeed releases lornoxicam at acidic pH (simulating the pH conditions in the stomach), dissolution method II is employed.
Test Method
Apparatus: Ph. Eur. Dissolution test for solid dosage forms and USP XXIII <711> apparatus 2, equipped with Sotax AT7 and Perkin Elmer UV/VIS Spectrometer Lambda 2. The measurement was performed continuously using Perkin-Elmer Dissolution Software for Lambda Series UV/VIS Spectrometers Version 3.0/ JAN 94. The calculations were performed using the same software.

Glass fibre filter: Whatman GF/F
Dissolution medium: 900.0 ml dissolution medium
Number of revolutions: 50 rpm
Stirrer: Paddle
Temperature of dissolution medium: 37° C.±0.5° C.
Measuring time: Every 5 minutes after the start of the test (details appear from the following examples)
Analysis Method
Detection wavelength: $\lambda$=378 nm
Measuring equipment: UV/VIS—spectrophotometer, 1 cm cuvette Preraration of Reagents Dissolution medium: Weigh out 50.0 g of sodium chloride and measure out 141.6 ml of concentrated hydrochloric acid. Dissolve the chemical with distilled water and dilute to with distilled water.
Standards
Stock solutions: 2 stock solutions ($S_1$ and $S_2$) with a concentration of 200 µg/ml lornoxicam were prepared. Lornoxicam is dissolved in solvent for standards (cf. below).
Standards: 20.00 ml of each of the stock solutions is added to the reference vessel (cf. below).
Solvent for standards: 1.5% w/w aqueous sodium acetate solution: methanol (1:1 v/v)
Test Procedure
900 ml of dissolution medium are filled to each of the vessels (typically three or six vessels for the product and one vessel for reference solution). The medium is heated to 37° C.±0.5° C. The product to be tested (e.g. a granulate, pellets or a final composition) is placed in the vessel. In the last vessel, 20.0 ml of each of the stock solutions are added. The spindel is started, and the absorbance of the samples and standards is measured at 378 nm with zero setting towards the dissolution medium.

The percentage dissolved is measured over a suitable time interval.

DISSOLUTION METHOD III 0.1 N HCl/pH 7.3 (lornoxicam)

This dissolution method includes a change in pH to simulate the in vivo situation.

Test Method

Apparatus: Ph. Eur. Dissolution test for solid dosage forms and USP XXIII <711> apparatus 2, equipped with Sotax AT7 and Perkin Elmer UV/VIS Spectrometer Lambda 2. The measurement was performed continuously using Perkin-Elmer Dissolution Software for Lambda Series UV/VIS Spectrometers Version 3.0/JAN 94. The calculations were performed using the same software.

Glass fibre filter: Whatman GF/F

Dissolution medium: 750 ml of dissolution medium 1, after 1 hour 250 ml of dissolution medium 2 are added Number of revolutions: 50 rpm Stirrer: Paddle Temperature of dissolution medium: 37° C.±0.5° C.

Measuring times: Every 5 minutes after the start of the test (details appear from the following examples)

Analysis Method

Detection wavelength: $\lambda$=378 nm

Measuring equipment: UV/VIS—spectrophotometer, 1 cm cuvette

Preparation of Reagents

Dissolution media

Dissolution medium 1:0.1 N HCl

Dissolution medium 2: Weigh out 73,6 g trisodium phosphate, dodecahydrate ($Na_3PO_4$, $12H_2O$) and measure out 31,8 ml 0,1 N sodium hydroxide. Dissolve the chemicals in distilled water and dilute to 1000,0 ml with distilled water.

Standards

Stock solutions: 2 stock solutions ($S_1$ and $S_2$) with a concentration of 200 µg/ml lornoxicam were prepared. Lornoxicam is dissolved in solvent for standards (cf. below).

Standards: 20.00 ml of each of the stock solutions are added to the reference vessel (cf. below).

Solvent for standards: 1.5% w/w aqeous sodium acetate solution:methanol (1:1 v/v)

Test Procedure 750 ml of dissolution medium 1 are filled to each of the vessels (typically three or six vessels for the product and one vessel for reference solution). The medium is heated to 37° C.±0.5° C. The product to be tested (e.g. a granulate, pellets or a final composition) is placed in the vessel. In the last vessel, 20.0 ml of each of the stock solutions are added. The spindel is started. After 1 hour 250 ml of dissolution medium 2 (37° C.±0.5° C.) are added.

The absorbance of the samples and standards is measured at 378 nm with zero setting towards the dissolution medium.

The percentage dissolved is measured over a suitable time interval.

DISSOLUTION METHOD IV 0.1 N HCl/pH 7.4 (lornoxicam)

This dissolution method includes a change in pH to simulate the in vivo situation. Furthermore, this dissolution method has been employed in experiments performed in order to clarify whether a pre-treatment of the product in 0.1 N hydrochloric acid has any influence on the results obtained afterwards in a dissolution medium having a pH of 7.4.

Test Method

Apparatus: Ph. Eur. Dissolution test for solid dosage forms and USP XXIII <711> apparatus 2, equipped with Sotax AT7 and Perkin Elmer UV/VIS Spectrometer Lambda 2. The measurement was performed continuously using Perkin-Elmer Dissolution Software for Lambda Series UV/VIS Spectrometers Version 3.0/JAN 94. The calculations were performed using the same software.

Glass fibre filter: Whatman GF/F

Dissolution medium: 750 ml of dissolution medium 1, after 1 hour the medium is changed to 900 ml of dissolution medium 2.

Number of revolutions: 50 rpm

Stirrer: Paddle

Temperature of dissolution medium: 37° C.±0.5° C.

Measuring times: Every 5 minutes after the start of the test (details appear from the following examples)

Analysis Method

Detection wavelength: $\lambda$=378 nm

Measuring equipment: UV/VIS—spectrophotometer, 1 cm cuvette

Preparation of Reagents

Dissolution media:

Dissolution medium 1:0.1 N HCl

Dissolution medium 2: Distilled water containing 10.1 mg/ml of sodium hydrogenphosphate dihydrate ($Na_2HPO_4$ $2H_2O$) and 1.6 mg/ml of sodium dihydrogenphosphate monohydrate ($NaH_2PO_4$ $H_2O$)

Standards

Stock solutions: 2 stock solutions ($S_1$ and $S_2$) with a concentration of 200 µg/ml lornoxicam were prepared. Lornoxicam is dissolved in solvent for standards (cf. below).

Standards: 20.00 ml of each of the stock solutions is added to the reference vessel (cf. below)

Solvent for standards: 1.5% w/w aqueous sodium acetate solution:methanol (1:1 v/v)

Test Procedure 750 ml of dissolution medium 1 are filled to each of the vessels (typically three or six vessels for the product and one vessel for reference solution). The medium is heated to 37° C.±0.5° C. The product to be tested (e.g. a granulate, pellets or a final composition) is placed in the vessel. In the last vessel, 20.0 ml of each of the stock solutions are added. The spindel is started. After 1 hour the medium is decanted carefully and the medium is discarded. To the remaining product in the vessel 900 ml of dissolution medium 2 (37° C.±0.5° C.) are added. The absorbance of the samples and standards is measured at 378 nm with zero setting towards the dissolution medium employed.

The percentage dissolved is measured over a suitable time interval.

DISSOLUTION METHOD V pH 7.3 (lornoxicam)

This dissolution method was used to inter alia clarify the influence of pH and/or the specific dissolution medium on the release rate and also to clarify, if the results obtained at pH 7.3—without any pre-treatment in 0.1 N hydrochloric acid—were different from those obtained with pre-treatment in 0.1 N hydrochloric acid.

The buffer capacity of the dissolution medium employed was investigated to ensure a sufficient capacity. pH in the medium was measured before a product was added and after the end of the test. Both measurements revealed the same pH value (7.28), i.e. the buffer capacity is sufficient.

Test Method

Apparatus: Ph. Eur. Dissolution test for solid dosage forms and USP XXIII <711> apparatus 2, equipped with Sotax AT7 and Perkin Elmer UV/VIS Spectrometer Lambda 2. The measurement was performed continuously using Perkin-Elmer Dissolution Software for Lambda Series UV/VIS Spectrometers Version 3.0/JAN 94. The calculations were performed using the same software.

Glass fibre filter: Whatman GF/F

Dissolution medium: 750 ml of the dissolution medium 1 and 250 ml of dissolution medium 2, the resulting pH is 7.3

Number of revolutions: 50 rpm

Stirrer: Paddle

Temperature of dissolution medium: 37° C.±0.5° C.

Measuring times: Every 5 minutes after the start of the test (details appear from the following examples)

Detection wavelength: $\lambda$=378 nm

Measuring equipment: UV\VIS—spectrophotometer, 1 cm cuvette

Preparation of Reagents

Dissolution media:

Dissolution medium 1: 0.1 N HCl

Dissolution medium 2: Weigh out 73,6 g trisodium phosphate dodecahydrate ($Na_3PO_4 \cdot 12H_2O$) and measure out 31,8 ml 0,1 N sodium hydroxide. Dissolve the chemicals in distilled water and dilute to 1000,0 ml with distilled water.

Standards

Stock solutions: 2 stock solutions ($S_1$ and $S_2$) with a concentration of 200 $\mu$g/ml lornoxicam were prepared. Lornoxicam is dissolved in solvent for standards (cf. below).

Standards: 20.00 ml of each of the stock solutions is added to the reference vessel (cf. below).

Solvent for standards: 1,5% sodium acetate solution:methanol (1:1)

Test Procedure 750 ml of the dissolution medium 1 and 250 ml of dissolution medium 2 are filled to each of the vessels (typically three or six vessels for the product and one vessel for reference solution). The medium is heated to 37° C.±0.5° C. The product to be tested (e.g. a granulate, pellets or a final composition) is placed in the vessel. In the last vessel, 20.0 ml of each of the stock solutions are added. The spindel is started. The absorbance of the samples and standards is measured at 378 nm with zero setting towards the dissolution medium.

The percentage dissolved is measured over a suitable time interval.

Calculation for all Methods

Percentage dissolved was calculated with reference to an external standard in the reference vessel.

The concentration of the standard in the reference vessel is calculated by the formula below:

$$\text{mg lornoxicam per 1000 ml} = \left(\frac{q_1 \cdot 20}{V} + \frac{q_2 \cdot 20}{V}\right) \cdot \frac{1000}{940}$$

Where:

$q_1$ = amount of standard weighed out for $S_1$ (mg)

$q_2$ = amount of standard weighed out for $S_2$ (mg)

20 = added volume of $S_1$ and $S_2$ to the referenced vessel (ml)

$V$ = dilution volume of the standard (ml)

940 = volume in the reference vessel after addition of the standards ($S_1$ and $S_2$) to the vessel (ml)

1000 = conversion factor to 1000 ml

The content of lornoxicam as percentage dissolved was calculated from the formula below:

$$\frac{abs_{sample} \cdot StA \cdot V \cdot 100}{abs_{StA} 1000 \cdot u} \cdot \frac{n}{100}$$

Where $abs_{sample}$ = absorbance measured in each vessel containing samples $StA$ = mg lornoxicam pr 1000 ml in the vessel containing standard $V$ = volume of the medium (ml)

100 = factor converting to percent $abs_{StA}$ = absorbance measured in vessel containing the standard $u$ = declared content (mg)

$n$ = potency of the standard (%)

100 = factor converting to percent

1000 = factor converting the concentration of the standard to mg/ml

The following examples are intended to illustrate specific embodiments of the present inventions but are not intended in any way to limit the invention.

EXAMPLES

The following Examples 1–8 relate to the preparation of various cores containing lornoxicam as an example of an NSAID substance. Example 9 relates to the preparation of a quick release granulate, Examples 10–17 illustrate inter alia the influence of the composition of the pellets or the coat on the release rate and Example 18 relates to an immediate release composition disclosed in EP-A-0 438 249.

Example 1

Preparation of Cores Containing Lornoxicam and Coating of the Cores with a CR Coating Batch Nos. 04029831 (uncoated pellet cores) and 05029833 (coated pellet cores) were prepared.

Lornoxicam pellet cores were prepared by manufacturing of pellet cores and subsequent coating with an inner and an outer coat.

The pellet cores were prepared by the use of an extrusion/spheronization technique.

The ingredients are listed in Table 1. The ingredients I and II were mixed in a beaker by stirring, wetted with 150 g water and then mixed to a homogenous mass. The ingredients III to VII were filled into a Moulinex laboratory size mixer and mixed for 5 min, whereafter the homogenous mass was added and mixed. The beaker was rinsed with the remaining water and added to the mixer.

TABLE 1

| Ingredients | Amount (g): |
|---|---|
| I Lornoxicam | 54 |
| II Polysorbate 20 | 54 |
| III Cellulose, microcrystalline | 102 |
| IV Lactose | 315 |
| V Carmellose sodium | 3 |
| VI Maltodextrin | 12 |
| VII Pregelatinized starch | 60 |
| VIII Purified water | 150 + 18 |

The resulting mass was extruded in a Nica E 140 extruder with a screen size of 0.6 mm. The extrudate was spheronized in a laboratory size spheronizer at a rotation speed of 700 rpm for 4 min. The pellet cores thus produced were dried in a laboratory size fluid bed dryer with an inlet temperature of approximately 40° C., and the drying process was continued until the outlet temperature has reached approximately 30° C. The total drying time was approximately 25 min.

The dried pellet cores were fractionated in a Retsch sieving apparatus with a lower screen of 0.5 mm and an upper screen of 0.8 mm.

The release of lornoxicam from the pellet cores obtained was determined by dissolution method I (pH 7.4) and is as follows:

| Time | Release (%) |
|---|---|
| 10 min. | 52.1 |
| 1 h | 97.6 |

Thus, the relase of lornoxicam from the uncoated pellets is rapid and is almost accomplished within about 1 hour.

100 g of these pellet cores were coated with an inner coat and an outer coat in a laboratory size bottom spray fluid bed coater with a spray pressure of 1 bar for both the inner coat and the outer coat. The temperature of the coating process was maintained at an inlet temperature of approximately 35° C. to 40° C.

The composition of the coating is shown in Table 2:

TABLE 2

| Ingredient | Amount (g) |
|---|---|
| Inner coat | |
| Hypromellose (Methocel E prem) | 3.25 |
| Magnesium stearate | 0.68 |
| Talc | 6.07 |
| Eudragit NE 30 D | 216 |
| Purified water | 274 |

TABLE 2-continued

| Ingredient | Amount (g) |
|---|---|
| Outer coat | |
| Hypromellose (Methocel E5 prem) | 4.0 |
| Talc | 4.0 |
| Purified water | 96.0 |

In the coating process the following amount of inner and outer coat was applied. The amount of dry matter applied calculated in percentage of the pellet core weight also appears from the below:

Inner coat: 35.9 g coating solution (corresponding to a dry matter content of approximately 5.5% w/w of the pellet core weight)

Outer coat: 12.5 g coating solution (corresponding to a dry matter content of approximately 1% w/w of the pellet core weight)

After the application of the coatings, the coated pellet cores were cured at a bed temperature of approximately 70° C. for 30 min, whereafter the coated pellet cores were cooled to a bed temperature below 35° C.

After the coating, the coated pellet cores are screened through a 1.2 mm screen. Oversized material is discarded.

Example 2

Preparation of Pellet Cores According to the Invention Leaving Out a Surface Active Substance from the Cores Batch No. 09029831 (uncoated pellet cores) was prepared.

Lornoxicam pellet cores were prepared by using the ingredients listed in Table 3.

TABLE 3

| Ingredients | Amount (g) |
|---|---|
| I Lornoxicam | 27 |
| II Cellulose, microcrystalline | 54 |
| III Lactosemonohydrate | 216 |
| IV Carmellosesodium | 3 |
| V Purified water | 84 |

The pellet cores were prepared by the use of the extrusion/spheronization technique as described in Example 1, wherein the ingredients I to IV were mixed for 5 min in a Moulinex laboratory size mixer, whereafter the ingredients V was added.

The release of lornoxicam from pellet cores was determined by dissolution method I (pH 7,4) and is as follows:

| Time | Release (% w/w) |
|---|---|
| 10 min | 19.1 |
| 1 h | 69.8 |

From the dissolution data given above it is seen that the release is not accomplished after 1 hour and compared with the result obtained with the uncoated pellet cores in Example 1 it seems as if the inclusion of a surface active agent like e.g. polysorbate 20 has a significant influence on the dissolution rate.

Example 3

Preparation of Pellet Cores Corresponding to the Pellets in Example 1 but in a Smaller Batch Size Batch No. 09029832 (uncoated pellet cores) was prepared.

This Example is intended to illustrate any relevant variation which may turn up as a dependency of the batch size.

Lornoxicam pellet cores were prepared as described in Example 1 with the exception that in Example 3, the amounts of the ingredients listed in Table 4 were used.

TABLE 4

| Ingredients | Amount (g) |
|---|---|
| I Lornoxicam | 27 |
| II Polysorbate 20 | 27 |
| III Cellulose, microcrystalline | 51 |
| IV Lactose | 157.5 |
| V Carmellose sodium | 1.5 |
| VI Maltodextrin | 6 |
| VII Pregelatinized starch | 30 |
| VIII Purified water | 60 + 15 |

The release of lornoxicam from these pellets cores was determined by dissolution method I (pH 7.4) and is as follows:

| Time | Release (% w/w) |
|---|---|
| 10 min | 61.2 |
| 1 h | 98.0 |

Thus, the pellet cores prepared have the same dissolution behaviour as the pellet cores prepared in Example 1, i.e. the batch size seems to be without any significant influence on the release rate.

Example 4

Preparation of Coated Pellet Cores Having a Thinner Inner Coating than the Coated Pellet Cores of Example 1

Batches Nos 11029831 (uncoated pellet cores) and 20029832 (coated pellet cores) were prepared.

Lornoxicam pellet cores were prepared as described in Example 1 with the exception that in Example 4, the amounts of the ingredients listed in Table 5 were used.

TABLE 5

| Ingredients | Amount (g) |
|---|---|
| I Lornoxicam | 27 |
| II Polysorbate 20 | 27 |
| III Cellulose, microcrystalline | 51 |
| IV Lactose | 157.5 |
| V Carmellose sodium | 1.5 |
| VI Maltodextrin | 6 |
| VII Pregelatinized starch | 30 |
| VIII Purified water | 51 + 15 |

The release of lornoxicam from these pellets cores was determined by dissolution method I (pH 7.4) and is as follows:

| Time | Release (% w/w) |
|---|---|
| 10 min | 63.8 |
| 1 h | 100.7 |

Accordingly, the release of lornoxicam from the pellet cores is accomplished within 1 hour.

The pellet cores were coated as described in Example 1 with the exception that in Example 4, 100 g pellet cores were coated with an amount of inner and outer coat as follows:

Inner coat: 20.0 g coating solution (corresponding to a dry matter content of approximately 3% w/w of the pellet core weight).

Outer coat: 12.5 g coating solution (corresponding to a dry matter content of approximately 1% w/w of the pellet core weight).

As appears from the above, the amount of dry matter of the inner coat is smaller than in Example 1, whereas the amount of dry matter of the outer coat is the same as in Example 1. Accordingly, it is expected that the release of lornoxicam from the coated pellets of Example 4 is faster than that of lornoxicam from the coated pellets of Example 1.

Example 5

Preparation of Pellet Cores Corresponding to Those of Example 3 with the Exception that the Surface Active Agent is Replaced by Lactose Batch No. 11029834 (uncoated pellet cores) was prepared.

Lornoxicam pellet cores were prepared as described in Example 2 with the exception that in Example 5, the ingredients listed in Table 6 were used. Compared with the above Example 3 it is seen that the composition of pellet cores of Example 5 is very similar to those of Example 3, the only differences are that in the pellet cores of Example 3 a surface active agent (polysorbate 20) is included and the amount of water employed differs a little.

TABLE 6

| Ingredients | Amount (g) |
|---|---|
| I Lornoxicam | 27 |
| II Cellulose, microcrystalline | 51 |
| III Lactose | 184.5 |
| IV Carmellose sodium | 1.5 |
| V Maltodextrin | 6.0 |
| VI Pregelatinized starch | 30.0 |
| VII Purified water | 84.0 |

The release of lornoxicam from these pellets cores were determined by dissolution method I (pH 7.4) and is as follows:

| Time | Release (% w/w) |
|---|---|
| 10 min | 20.5 |
| 1 h | 62.4 |

In conclusion the same pattern is observed as in Example 2, namely that the exclusion of a surface active agent has a decreasing effect on the release rate of lornoxicam from the pellet cores.

Example 6

Preparation of Pellet Cores Having a Content of a Disintegrant

Batch No. 19029834 (uncoated pellet cores) was prepared.

Lornoxicam pellet cores were prepared by using the extrusion/spheronization technique as described in Example 1. However, the ingredients used in Example 6 are listed in Table 7:

TABLE 7

| Ingredients | Amount (g) |
| --- | --- |
| I Lornoxicam | 27 |
| II Polysorbate 20 | 27 |
| III Cellulose, microcrystalline | 51 |
| IV Lactose | 142.5 |
| V Carmellose sodium | 1.5 |
| VI Maltodextrin | 6 |
| VII Pregelatinized starch | 30 |
| VIII Croscarmellose sodium | 15 |
| IX Purified water | 51 + 15 + 15 |

The ingredients I and II were mixed in a beaker, wetted with 51 g water and then mixed to a homogeneous mass. The ingredients III to VIII were added to a Moulinex laboratory size mixer and mixed for 5 min, whereto the homogeneous mass was added and mixed. The beaker was rinsed with 2×15 g water and added to the mixer.

The extrudation and spheronizing procedure were performed as described in Example 1.

The release of lornoxicam from the pellet cores was determined by dissolution method II (0.07 N HCl) and is as follows:

| Time | Release (% w/w) |
| --- | --- |
| 1 h | 5.7 |

Thus, only a very small amount of the lornoxicam present in the pellets is released at a pH corresponding to that of 0.07 N HCl. The inclusion of an disintegrant such as, e.g., croscarmellose sodium does not seem to have any increasing effect on the release rate of lornoxicam from the pellet cores. Furthermore, uncoated cores containing lornoxicam do not seem to be a suitable choice in order to obtain a relatively fast release of lornoxicam at low pH like the conditions in the stomach.

Example 7

Preparation of Pellet Cores—Modification of the Composition of the Pellets in Order to Influence the Release Rate of Lornoxicam Batch No. 19029836 (uncoated pellet cores) was prepared.

Lornoxicam pellet cores were prepared. The ingredients used are listed in Table 8.

TABLE 8

| Ingredients | Amount (g) |
| --- | --- |
| I Lornoxicam | 7.5 |
| II Sodium bicarbonate | 37.7 |
| III Cellulose, microcrystalline | 90.4 |
| IV Dibasic Calcium Phosphate, Anhydrous | 104.1 |
| V Low-substituted Hydroxypropyl Cellulose | 45.3 |
| VI Hydroxypropylcellulose | 15 |
| VII Purified water | 115.8 |
| VIII Ethanol 99.9% | 38.7 |

The ingredients II to IV were mixed in a Moulinex laboratory size mixer and mixed for 5 min. To 100 g of this mixture ingredient I was added and mixed in a cubus mixer for 5 min. The resulting mass was screened through a 0.5 mm screen and returned to the Moulinex mixer and mixed for further 6 min. A premixed mixture of ingredient VII and VII was added to the powder mixture and massed for 6 min.

The resulting mass was then extruded and spheronized according to the method II described in Example 1.

The release of lornoxicam from the pellet cores was determined by dissolution method II (0.07 N HCl) and is as follows:

| Time | Release (% w/w) |
| --- | --- |
| After 1 h | 37.8 |

The release of lornoxicam from the pellets is significantly increased compared with the pellets of Example 6, but still not quite satisfactory.

Example 8

Preparation of Pellets Coated with a Coating Having Varying Amounts of a Hydroxypropylmethylcellulose (HPMC)

Batch No. 23029833 (uncoated pellets) was prepared

Lornoxicam pellet cores were prepared as described in Example 4 and with the same composition.

The release of lornoxicam from the pellet cores was determined by dissolution method III (0.1 N HCl followed by pH 7.3) for 3 hours (i.e. 1 hour at a pH corresponding to the pH of 0.1 N HCl and 2 hours at pH 7.3) and is as follows:

| Time | Release (% w/w) |
| --- | --- |
| 10 min | 36.9 |
| 1 h | 37.2 |
| 1 + 1 h: | 86.4 |
| 1 + 2 h: | 95.7 |

Thus, the release in 0.1 N HCl is not very high (most of the lornoxicam which releases in 0.1 N HCl is released within the first 10 min) and the release rate is certainly not fast enough to anticipate that lornoxicam is released in vivo sufficiently fast to lead to a therapeutic effect.

In the following, two different batches of coated pellets of 100 g each were prepared.

Batch 1 (Batch No. 24029832-coated pellet cores):

100 g pellet cores were coated according to the procedure described in Example 1. The composition of the coating is as follows:

| Ingredients | Amount (g) |
| --- | --- |
| Inner coat | |
| Hypromellose (Methocel E5 prem) | 11.3 |
| Magnesium stearate | 0.6 |
| Talc | 5.4 |
| Eudragit NE 30 D | 191.7 |
| Purified water | 291 |
| Outer coat | |
| Hypromellose (method E % prem) | 4.0 |
| Talc | 4.0 |
| Purified water | 96.0 |

The following amount of inner and outer coat was used:

Inner coat: 20.1 g coating solution (corresponding to a dry matter content of approximately 3% wow of the pellet core weight; the HPMC content corresponds to 15.1% w/w).

Outer coat: 12.5 g coating solution (corresponding to a dry matter content of approximately 1% w/w of the pellet core weight).

Batch 2 (Batch No., 26029832-coated pellet cores):

100 g pellet cores were coated as described in Example 1. The composition of the coating is as follows:

| Ingredients | Amount (g) |
| --- | --- |
| Inner coat | |
| Hypromelose (Methocel E5 prem.) | 3.74 |
| Magnesium stearate | 0.17 |
| Talc | 1.48 |
| Eudragit NE 30 D | 31.9 |
| Purified water | 62.7 |
| Outer coat | |
| Hypromellose (method E % prem) | 4.0 |
| Talc | 4.0 |
| Purified water | 96.0 |

The following amount of inner and outer coat was used:

Inner coat: 20.1 g coating solution (corresponding to a dry matter content of approximately 3% w/w of the pellet core weight; the HPMC content corresponds to 25% w/w).

Outer coat: 12.5 g coating solution (corresponding to a dry matter content of approximately 1% w/w of the pellet core weight).

Example 9

Preparation of a Quick Release Granulate Containing Lornoxicam

Batch No. 972510 (granulate) was prepared.

A granulate containing lornoxicam were prepared by using the ingredients listed in Table 9. The composition of the granulate is essentially the same as that of the pellet cores of Example 7. The granulate was prepared in order to investigate whether it is possible to achieve a faster release of lornoxicam from a granulate than from pellet cores. From the results given below it is seen that the step of preparing pellets from a particulate composition containing lornoxicam has a dramatically decrease on the release rate of lornoxicam from the composition.

TABLE 9

| | Ingredients | Amount (kg) |
| --- | --- | --- |
| I | Lornoxicam | 2.00 |
| II | Sodium hydrogencarbonate | 10.00 |
| III | Cellulose microcristalline | 24.00 |
| IV | Calcium hydrogen phosphate anhydrous | 27.60 |
| V | Hydroxy Propyl Cellulose | 4.00 |
| VI | Low-Substituted Hydroxy Propyl Cellulose | 12.00 |
| VII | Purified water | 27.00 |
| VIII | Ethanol 96% | 9.00 |
| IX | Calcium stearate | 0.40 |

Ingredients II, III IV, V and VI were added to a Diosna intensive mixer and mixed for 1 min with the impeller speed I and chopper speed I. Out of this mixture, 10 kg was added the ingredient I by sieving through a Quadro Comil U20 with the sieve 062R in the following way: A part of the 10 kg mixture was sieved followed by ingredient I, whereafter the remaining of the 10 kg mixture was sieved. Ingredient I was not added to the mixture and mixed in the Diosna mixer for approximately 1 min.

A mixture of ingredient VII and VIII was added to the Diosna mixer, whereafter the granulation was started for 6 min with impeller speed I and with no use of the chopper.

After the granulation, the granulate was dried in a fluid bed until the outlet temperature had reached approximately 50° C. and water content was below 1.0%, determined as LOD (Loss on Drying) when a sample of approximately 10 g was heated to a temperature of 70° C. in 30 min. The granulate was sieved through a 0.71 sieve using a Frewitt siever. Oversized material was discarded.

Ingredient IX was sieved in the Quadro Comil with a sieve 062R and an equal amount of the granulate described above was added and mixed. This mixture was mixed with the remaining of the granulate in the Diosna mixer for 25 sec with an impeller speed of I and without using the chopper.

This mixture was compressed into a 9,5 mm concave tablets with a hardness of 80 to 100 N (the compression of the granulate was performed in order to avoid any of the problems which could arise during dissolution testing of a granulate and which are related to such bad wetting properties of a granulate that the granulate would float on the top of the dissolution medium giving rise to a in vitro unsatisfactory release of lornoxicam. However, later results have shown that granulates prepared in accordance with the above have suitable wetting properties, i.e. the final step of compression before dissolution testing is not necessary.

The dissolution of tablet cores was determined by the dissolution method II (0.07 N HCl) and is as follows:

| Time | Release (% w/w) |
| --- | --- |
| 20 min | 100.6 |

The disintegration time of the tablets tested was at the most about 5 min. Thus, the dissolution rate of the granulate is expected to be of the same or quicker order of magnitude.

The release data given above are most surprising and give evidence that a fast release fraction containing a drug substance which is almost insoluble under acidic conditions can only be obtained if the composition is designed to a very fast release. In other words, application of traditionally prepared granulates and/or compositions made from such traditional granulates or particulate formulations do not seem to release the drug substance sufficiently fast under acidic conditions as those prevailing in the stomach. Accordingly, such traditional compositions are expected to release only a minor amount of the drug substance in the stomach and to release the remaining amount of lornoxicam in the intestines, i.e. after the composition reaches the intestines 1–3 hours after intake.

Compared with the dissolution data given in Example 7 a dramatically increase in dissolution rate is observed for the granulate compared with the pellet cores. Thus, in order to achieve a very fast release of lornoxicam from a composition it seems as if the fast fraction advantageously may be constituted by a granulate rather than uncoated pellet cores or film-coated pellet cores.

Conclusion with Respect to Examples 1–9

In the preceding examples it has been shown that pellets cores cannot release lornoxicam very quickly at pH 7,4 unless a surfactant is added (Examples 2 and 5), even though lornoxicam is soluble at pH 7,4. When a surfactant, e.g. polysorbate 20, was added the release at pH 7,4 was acceptable from the point of view that the core can enter an once daily formulations without significantly controlling the dissolution rate (Examples 1, 3 and 4). This control should ideally be taken care of by the applied lacquer.

When these pellet cores were analyzed with respect to dissolution behaviour under acidic conditions in which lornoxicam is only slightly soluble a satisfactory release was not obtained even if a surfactant was used (Examples 6 and 8). Therefore, another kind of subunits have to be used for the relatively fast releasing fraction. Subunits in the form of a granulate and with the composition as described in Example 9 seem to give a satisfactory fast release. However, subunits with the same formulation as in Example 9, but in the form of pellet cores, will not give a satisfactory release rate in acidic conditions as shown in Example 7.

Example 10

Preparation of a Composition Containing a Mixture of Uncoated and Coated Pellet Cores The following example illustrate the dissolution behaviour of a composition containing a mixture of uncoated and coated pellet cores. The uncoated pellets are intended to simulate a fast release fraction and the coated pellets are intended to simulate a delayed release fraction.

Coated pellets obtained according to Example 1 were mixed with pellet cores obtained according to Example 4 and the final composition contained 40% of uncoated pellet cores and 60% coated pellets (the percentage is given as % w/w of the total dose of lornoxicam in the composition, i.e. the uncoated fraction accounts for 40% w/w of the total content of lornoxicam whereas the coated fraction accounts for 60% w/w of the total content of lornoxicam. A unit dosage form of the composition contains 8 mg of lornoxicam.

The dissolution test was carried out according to dissolution method III. The following dissolution data were obtained:

| Time (h) | 11029831 (uncoated fraction) + 05029833 (coated fraction) (5.5/4.3)[a] Release (% w/w) |
| --- | --- |
| 0 | 0 |
| 0.5 | 1.4 |
| 1 | 2.9 |
| 2 | 38.4 |
| 3 | 46.1 |
| 4 | 49.6 |
| 5 | 53.5 |
| 6 | 55.9 |
| 7 | 59 |
| 8 | 61.4 |
| 9 | 64.6 |
| 10 | 67.2 |
| 11 | 69.2 |
| 13 | 74 |
| 14 | 75.6 |
| 15 | 77.9 |
| 16 | 79.3 |
| 17 | 80.7 |
| 18 | 82.5 |
| 19 | 83.6 |
| 20 | 85.3 |
| 21 | 86.4 |
| 22 | 87 |
| 23 | 88.1 |
| 24 | 89 |

[a](5.5/4.3) relates to the fact that the content of dry matter in the coat is 5.5% w/w and the HPML content is 4.3% w/w.

From the data given above it is seen that only 2.9% w/w lornoxicam is released after 1 hour. Thus, the "fast release fraction", i.e. the uncoated pellets, is not able to release all its content of lornoxicam under acidic conditions and during the first hour of the test. If this was the case, a release of about 40% is to be expected after 1 hour.

A dramatically increase in dissolution is observed after 2 hours reflecting the pH change of the dissolution medium 1 hour after the start of the test. Furthermore, a retardation of the release of lornoxicam is observed at pH 7.4 compared with the uncoated pellets cores, i.e. the coating is in control of the release rate. However, a composition containing a mixture of uncoated and coated pellets does not seem to enable a fast release of lornoxicam. Therefore, the fast release fraction has to been manipulated in some way in order to release the active substance (lornoxicam) faster.

Example 11

Preparation of a Composition Containing a Mixture of a Quick Release Granulate and a Delayed Release Fraction of Coated Pellet Cores The composition described below was prepared in order to investigate the influence on the overall release rate of the granulate prepared in Example 9 which seems to have favourable properties with respect to a quick and very fast release of lornoxicam even under acidic conditions.

Coated pellets obtained according to Example 4 were mixed with a granulate obtained according to Example 9, where the mixture contained 40% w/w of the total dose of lornoxicam in the form of the granulate and the remaining 60% w/w of the total dose of lornoxicam was in the form of coated pellets (the concentration of lornoxicam in the granulate is about 2–3% w/w and about 9% w/w in the uncoated pellets). The dissolution test was carried out according to dissolution method III. The following dissolution data was obtained:

| Time (h) | 972510 (granulate) + 20029832 (coated pellets) (3/4.3) Release (% w/w) |
|---|---|
| 0 | 0 |
| 1 | 37.2 |
| 2 | 41.3 |
| 3 | 44.6 |
| 4 | 48.2 |
| 5 | 51.3 |
| 6 | 53.9 |
| 7 | 57 |
| 8 | 59.6 |
| 9 | 61.8 |
| 10 | 64.7 |
| 11 | 66.9 |
| 12 | 69.4 |
| 13 | 71.6 |
| 14 | 73.6 |
| 15 | 75.7 |
| 16 | 77.6 |
| 17 | 79.5 |
| 18 | 81.2 |
| 19 | 82.9 |
| 20 | 84.4 |
| 21 | 86 |
| 22 | 87.4 |
| 23 | 88.5 |
| 24 | 89.8 |

From the dissolution data given above, a fast release of lornoxicam is observed which is ascribed to the influence of the lornoxicam granulate.

In contrast to the results obtained in Example 10 a release of about 40% w/w of lornoxicam is observed after 1 hours. Thus, the above example gives evidence that a manipulation of the composition of the fast release fraction is necessary in order to achieve a suitable release even at a low pH. Furthermore, a delayed release is observed with respect to the coated pellets fraction.

Example 12

Investigation of the Controlled Release Lacquer Composition on the Overall Dissolution Rate Coated pellets obtained according to Example 8 (batch 1, 15% w/w HPMC in the coat was mixed with granulate obtained according to Example 9. The mixture contained 40% w/w of the total dose of lornoxicam in the form of the granulate, whereas the remaining 60% w/w of lornoxicam was in the form of coated pellets. The dissolution test was carried out according to dissolution method III. The following dissolution data was obtained:

| Time (h) | 972510 (granulate) + 24029832 (coated pellets) (3/15.1) Release (% w/w) |
|---|---|
| 0 | 0 |
| 0.5 | 35.7 |
| 1 | 35.7 |
| 2 | 43.2 |
| 3 | 50.0 |
| 4 | 55.8 |
| 5 | 60.9 |
| 6 | 66.2 |
| 7 | 70.7 |
| 8 | 74.4 |
| 9 | 78.3 |
| 10 | 81.5 |
| 11 | 84.8 |
| 12 | 87.3 |
| 13 | 89.3 |
| 14 | 91.1 |
| 15 | 92.6 |
| 16 | 93.8 |
| 17 | 95.0 |
| 18 | 95.9 |
| 19 | 96.6 |
| 20 | 97.2 |
| 21 | 97.5 |
| 22 | 97.8 |
| 23 | 98.0 |
| 24 | 97.5 |

From the dissolution data given above a much faster release of the delayed release fraction is observed compared with the results obtained in Example 11. Thus, the composition of the coat can be adjusted to a suitable release rate. In this example the content of HPMC in the coat is 15.1% w/w.

Example 13

Investigation of the Influence of the Composition of the Controlled Release Coat on the Release Rate Coated pellets obtained according to Example 8 (batch 2) were mixed with a granulate obtained according to Example 9. The mixture contained 40% w/w of the lornoxicam content in the form of the granulate and the remaining 60% w/w in the form of coated pellets. The dissolution test was carried out according to dissolution method III.

The following dissolution data was obtained:

| Time (h) | 972510 (granulate) + 26029832 (coated pellets) (3/25.0) Release (% w/w) |
|---|---|
| 0 | 0 |
| 0.5 | 37.3 |
| 1 | 37.3 |
| 2 | 58 |
| 3 | 69.1 |
| 4 | 79.9 |
| 5 | 87.6 |
| 6 | 92.6 |
| 7 | 95.9 |
| 8 | 97.8 |
| 9 | 98.9 |
| 10 | 99.3 |
| 11 | 99.4 |
| 12 | 99.4 |
| 13 | 99.4 |
| 14 | 99.4 |
| 15 | 99.5 |

After 6 hours 92.6% w/w is released whereas only 69.4% w/w was released in Example 12. Thus, the increase of the concentration of HPMC in the coat (25% in the present example in contrast to 15% in Example 12) has an increasing effect on the release rate of lornoxicam from the composition.

Example 14

Determination of Release Rate of Lornoxicam From Controlled Release Pellets

Dissolution data from coated pellets from Examples 1, 4 and 8 (batches 1 and 2) were determined by dissolution method I (pH 7.4). The following data have been obtained.

| Time (h) | 05029833 (coated pellets) (5.5/4.3) Example 1 | 20029832 (coated pellets) (3.0/4.3) Example 4 | 24029832 (coated pellets) (3.0/15.1) Example 8, batch 1 | 26029832 (coated pellets) (3.0/25.0) Example 8, batch 2 |
|---|---|---|---|---|
| 0 | 0 | 0 | 0 | 0 |
| 0.5 | 6.9 | 10.1 | 17.3 | 32.7 |
| 1 | 12.1 | 16.9 | 29 | 52.6 |
| 2 | 20.3 | 28.5 | 49.5 | 82.1 |
| 3 | 28.1 | 39.7 | 67.2 | 96.9 |
| 4 | 35.4 | 50 | 81.6 | 101.9 |
| 5 | 42 | 58.9 | 91.5 | 102.9 |
| 6 | 49.1 | 69.1 | 98.5 | 103 |
| 7 | 55.2 | 76.2 | 102.1 | 103.2 |
| 8 | 60.7 | 82.2 | 103.9 | 102.9 |
| 9 | 65.6 | 86.9 | 104.8 | 102.9 |
| 10 | 69.9 | 90.5 | 105.2 | 103.1 |
| 11 | 73.7 | 93.4 | 105.5 | 102.9 |
| 12 | 77.2 | 93.4 | 105.5 | |
| 13 | 80.3 | 95.2 | 105.8 | |
| 14 | 82.6 | 97.7 | 105.5 | |
| 15 | 85 | 97.9 | 105.8 | |
| 16 | 87.1 | 98 | 105.8 | |
| 17 | 88.6 | 98.7 | 105.9 | |
| 18 | 89.9 | 98.8 | 105.9 | |
| 19 | 91.2 | 99 | 105.8 | |

Figure 3:
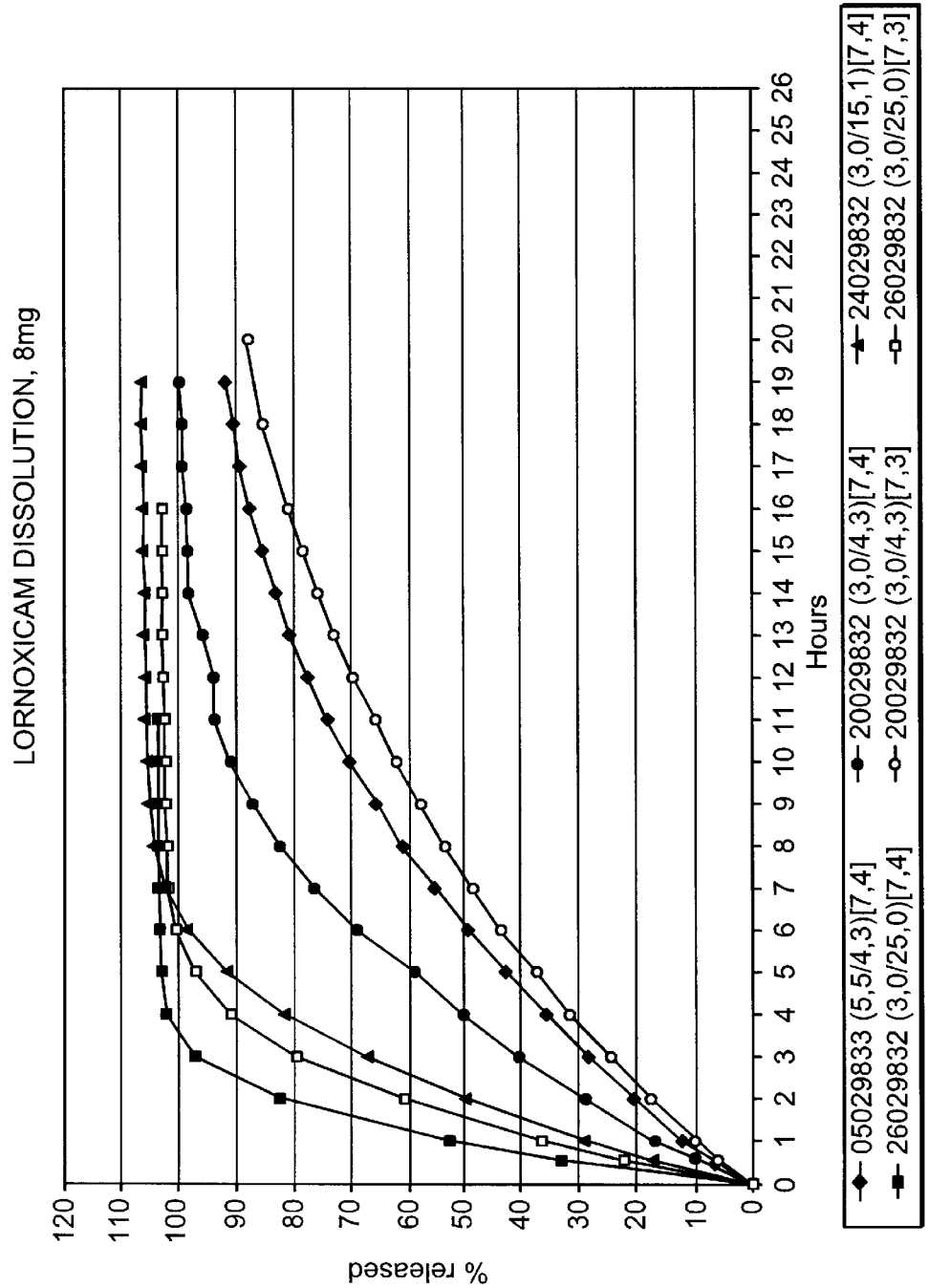
FIG. 3 shows dissolution profiles of lornoxicam compositions containing 8 mg of lornoxicam; further details are given in Examples 14 and 15 herein.

The data are also presented in FIG. 3. Comparison of the results obtained from the composition of Example 1 with that of Example 4 illustrates that the thickness of the CR (controlled release) coat influences the release rate in such a manner that a thinner coat leads to a more rapid release. The influence of HPMC as an example of a substance which is capable of forming pores in the coat on the release rate is illustrated by the release rate of the two different batches of Example 8 and the results reveal an increasing release rate when the concentration of HPMC increases.

Conclusion with Respect to Examples 10–14

In Examples 10–14, the preparation of a composition containing two fractions of subunits has been presented. One fraction representing a quick release part and the other fraction representing a controlled and delayed release part. Furthermore, the Examples illustrate the influence on the release rate of i) the composition of the quick release fraction and ii) composition and amount of lacquer applied on the controlled release fraction.

Example 15

Investigation of the Influence of the Dissolution Medium on the Release Rate Dissolution data from coated pellets from Examples 4 and 8 (batch 2) were obtained using dissolution method V (pH 7.3), and are as follows:

| Time (h) | 20029832 (coated pellets) (3.0/4.3)[7.3] Example 4 | 26029832 (coated pellets) (3.0/25.0)[7.3] Example 8, batch 2 |
|---|---|---|
| 0 | 0 | 0 |
| 0.5 | 6.2 | 22 |
| 1 | 10.1 | 36.1 |
| 2 | 17.3 | 60.7 |
| 3 | 24.3 | 79.2 |
| 4 | 30.9 | 90.7 |
| 5 | 36.9 | 96.9 |
| 6 | 42.9 | 100.1 |
| 7 | 48.2 | 101.4 |
| 8 | 53.1 | 101.9 |
| 9 | 57.6 | 102 |
| 10 | 61.8 | 102 |
| 11 | 65.7 | 102 |
| 12 | 69.3 | 102 |
| 13 | 72.4 | 102 |
| 14 | 75.4 | 102 |
| 15 | 78 | 102 |
| 16 | 80.3 | 102 |
| 18 | 84.3 | |
| 20 | 87.3 | |

The data are compared with the data from Example 14 in FIG. 3. An influence of the dissolution medium on the dissolution rate is observed, i.e. the choice of dissolution method is important (not only with respect to pH but also with respect to factors like, e.g., ionic strength, osmotic pressure etc.).

Example 16

Investigation of the Influence of a Pre-treatment in 0.1 N Hydrochloric Acid on the Dissolution Rate at pH 7.4

Dissolution data from coated pellets from Example 4 and Example 8 (batch 2) was determined by dissolution method I (pH 7.4) and method IV (1 hour at a pH corresponding to 0.1 N HCl and then at pH 7.4) and are as follows:

| Time (h) in pH 7.4 | 26029832 (3.0/25)(HCl/7.4) Example 8, batch 2 Dissolution method IV | 20029832 (3.0/4.3)(HCl/7.4) (HCl/7.4) Example 4, Dissolution method IV | 20029832 (3.0/4.3) Example 8 batch 2 Dissolution method I | 26029832 (3.0/25.0) Example 4, Dissolution method I |
|---|---|---|---|---|
| 0 | 0 | 0 | 0 | 0 |
| 0.5 | | | 10.1 | 32.7 |
| 1 | 47.6 | 16.9 | 16.9 | 52.6 |
| 2 | 77.5 | 29.1 | 28.5 | 82.1 |
| 3 | 92.4 | 39.6 | 39.7 | 96.9 |
| 4 | 98.1 | 48.3 | 50 | 101.9 |
| 5 | 100.2 | 56.9 | 58.9 | 102.9 |
| 6 | 100.6 | 64.8 | 69.1 | 103 |
| 7 | 100.6 | 71.6 | 76.2 | 103.2 |
| 8 | 100.7 | 77 | 82.2 | 102.9 |
| 9 | | | 86.9 | 102.9 |
| 10 | | 85.7 | 90.5 | 103.1 |
| 11 | | 88.8 | 93.4 | 102.9 |
| 12 | | 91.3 | 93.4 | |
| 13 | | 93.4 | 95.2 | |
| 14 | | 94.8 | 97.7 | |
| 15 | | 96 | 97.9 | |
| 16 | | 97 | 98 | |
| 17 | | 97.6 | 98.7 | |
| 18 | | 98.3 | 98.8 | |

-continued

| Time (h) in pH 7.4 | 26029832 (3.0/25)(HCl/7.4) Example 8, batch 2 Dissolution method IV | 20029832 (3.0/4.3)(HCl/7.4) (HCl/7.4) Example 4, Dissolution method IV | 20029832 (3.0/4.3) Example 8 batch 2 Dissolution method I | 26029832 (3.0/25.0) Example 4, Dissolution method I |
|---|---|---|---|---|
| 19 | | 98.6 | | 99 |

The dissolution results from Example 16 reveal that a pre-treatment with acid does not have any significantly influence on the rate of release from the delayed release fraction, i.e. the coated pellets fraction.

Figure 4:
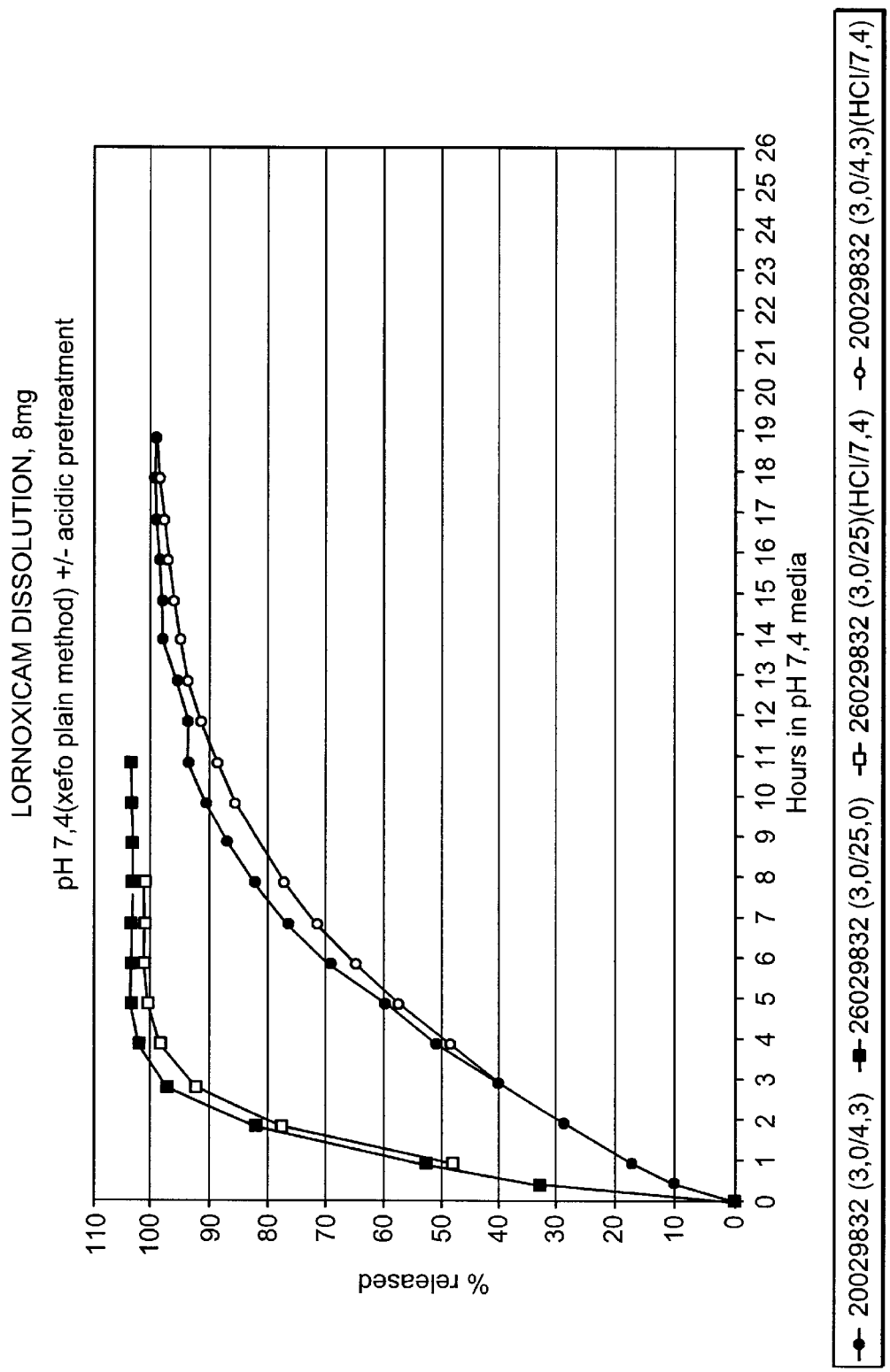
FIG. 4 shows dissolution profiles of compositions according to Example 15.

In FIG. 4 the data are presented and in order to make a proper comparison possible, the release data obtained by dissolution method IV have been displaced by 1 hour corresponding to the time period for treatment in 0.1 N HCl. Thus, in FIG. 4, the zero setting for all compositions is when the dissolution medium has a pH of 7.4. The observed differences with respect to the dissolution of lornoxicam from Example 1 and 4, respectively, are not significant and are within the standard deviation observed.

Conclusion with Respect to Examples 15 and 16

The results from Examples 15 and 16 have shown that coated pellets have the same release rate independent on whether a pre-treatment in acid has been included or not whereas a change in the dissolution method (from method I to method V) has a significant influence on the release rate.

Example 17

Investigation on the Influence of Dose on the Dissolution Rate

In this Example the dissolution profiles of a dose of 16 mg of lornoxicam are compared to a dose of 8 mg of lornoxicam. Dissolution profiles are obtained according to dissolution method III.

| Time (h) | 972510 + 24049832 8 mg Example 12 8 mg lornoxicam pr. capsule | 972510 + 24029832 Reanalysis of Example 12 (new sample) 8 mg lornoxicam pr. capsule | 972510 + 24029832 Reanalysis of Example 12 (new sample) 16 mg lornoxicam pr. capsule |
|---|---|---|---|
| 0 | 0 | 0 | 0 |
| 1 | 35.7 | 36.2 | 35.3 |
| 2 | 43.2 | 47 | 46.3 |
| 3 | 50.0 | 55.9 | 55 |
| 4 | 55.8 | 63.9 | 61.7 |
| 5 | 60.9 | 70.6 | 67.1 |
| 6 | 66.2 | 77.4 | 73.1 |
| 7 | 70.7 | 83 | 77.1 |
| 8 | 74.4 | 87.1 | 81.4 |
| 9 | 78.3 | 91.3 | 85.5 |
| 10 | 81.5 | 94.2 | 90.5 |
| 11 | 84.8 | 95.9 | 91.9 |
| 12 | 87.3 | 97.8 | 93.9 |
| 13 | 89.3 | 98.7 | 95.7 |
| 14 | 91.1 | 99 | 96.7 |
| 15 | 92.6 | 99.9 | 97.7 |
| 16 | 93.8 | 99.9 | 98.1 |
| 17 | 95.0 | 99.7 | 99 |
| 18 | 95.9 | 100.1 | 99.1 |
| 19 | 96.6 | | |
| 20 | 97.2 | | |
| 21 | 97.5 | | |
| 22 | 97.8 | | |
| 23 | 98.0 | | |
| 24 | 97.5 | | |

Figure 5:
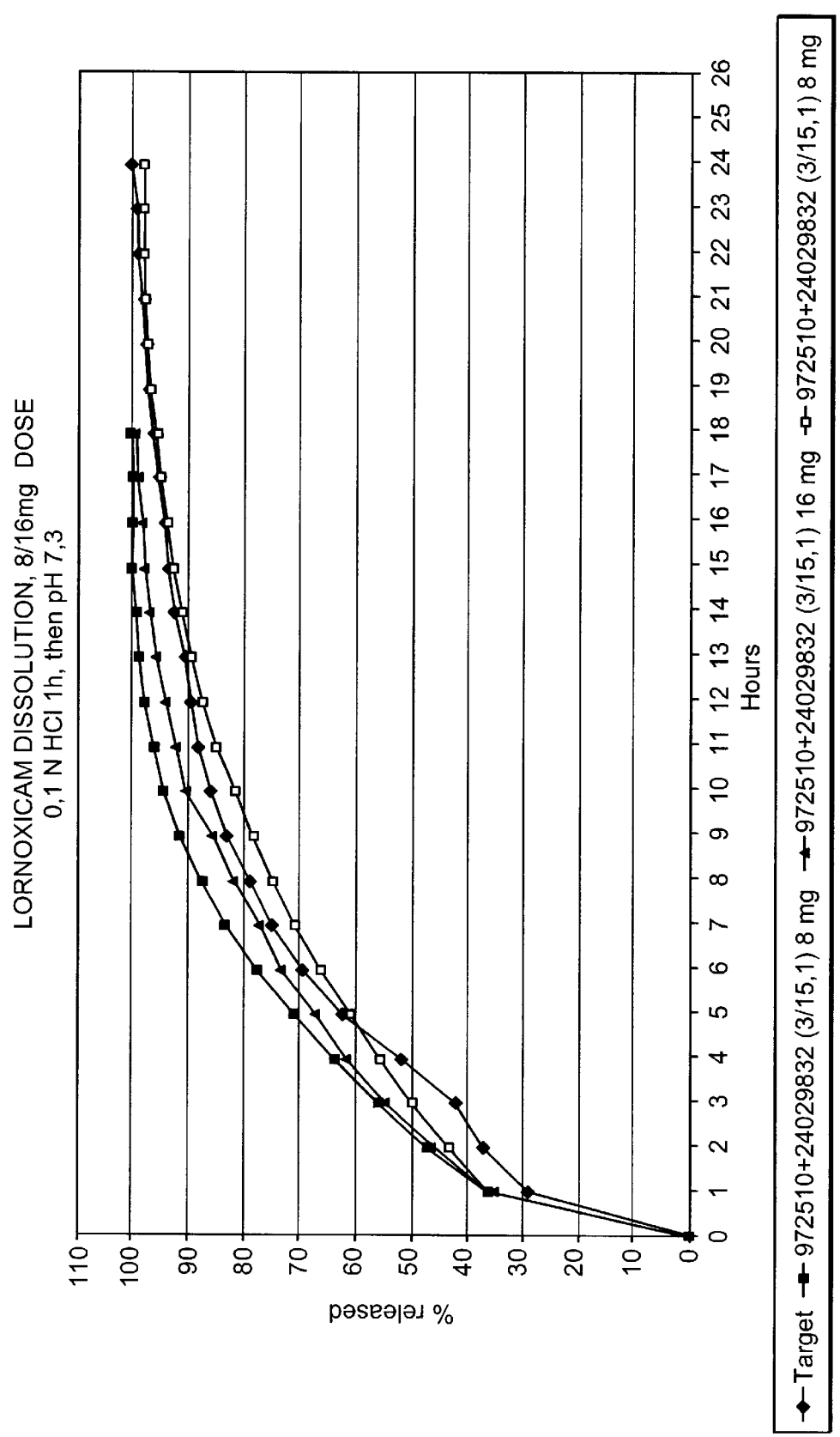
FIG. 5 shows dissolution profiles of compositions according to Example 17.

Dare presented in FIG. 5 and the curves show that the dose is without any significant influence on the release rate. In FIG. 5 a target profile calculated for lornoxicam has been included and it is seen that the compositions tested have profiles very close to the target profile.

Example 18

Investigation on Whether a Plain Granulate Quickly Releases an NSAID Substance

A granulate containing naproxen was prepared using the ingredients listed in Table 10.

The granulate was prepared in order to investigate whether a plain granulate like the one disclosed in EP-A-0 438 249A1 (ELAN Corporation P.L.C.) releases naproxen quickly (as defined herein) when the dissolution testing is done according to dissolution method II (n=2) described herein. No standards were used and, accordingly, a literature value for E(1%, 1 cm)=63 was used to calculate the content in the samples. The composition of the granulate corresponds to the one disclosed in Example 1 of EP-A-0 438 249A1 (ELAN Corporation P.L.C.).

TABLE 10

| Ingredients | Amount (g) |
|---|---|
| Naproxen | 232.0 |
| Polyvidone 30 | 7.2 |
| Isopropanol | 65.7 |

Naproxen and polyvidone 30 were mixed in a lab scale Kenwood mixer for 3 min. The mixture was granulated by slowly adding the isopropanol over a period of 2 min and the mixing was continued for 1 min. Then the granulate was dried on trays at 50° C. for 12 hours. Thereafter half of the granulate was sieved through a 500 μm sieve and the other half of the granulate was sieved through a 1000 μm sieve. Oversized material was discarded in both cases. The thus obtained two granulates were tested according to dissolution method II described herein.

Batch No. 26089831: 500 μm sieved granulate in an amount corresponding to a 150 mg tablet. In the following is given the results from the dissolution test.

| Time (h) | Release (dissolved naproxen) % w/w |
|---|---|
| 0 | 0 |
| 0.5 | 15 |
| 1 | 16.1 |
| 1.5 | 16.5 |
| 2 | 17.6 |

Batch No. 26089831: 1000 μm sieved granulate in an amount corresponding to a 150 mg tablet. In the following is given the results from the dissolution test.

| Time (h) | Release (dissolved naproxen) % w/w |
|---|---|
| 0 | 0 |
| 0.5 | 11.4 |
| 1 | 13.4 |
| 1.5 | 14.2 |
| 2 | 15.7 |

From the results given above, it is clear that such plain formulations do not release the NSAID substance very fast and, accordingly, such formulations or compositions do not fall under the definition of quick release defined herein (i.e. that at least about 50% of the NSAID substance is released within the first 20 min of the dissolution test).

What is claimed is:

1. An oral pharmaceutical modified release multiple-units composition in unit dosage form for administration of a therapeutically and/or prophylactically effective amount of a non-steroid anti-inflammatory drug substance, an NSAID substance, said unit dosage form comprising at least two NSAID-containing fractions,
   i) a first NSAID-containing fraction of multiple-units for quick release of the NSAID substance, wherein said fraction comprises an antacid or an alkaline agent and wherein the quick in vitro release is such that, when subjecting the first NSAID-containing fraction to dissolution method II employing 0.07 N HCl as dissolution medium, at least 50% w/w of the NSAID substance is released within the first 20 min of the test; and
   ii) a second NSAID-containing fraction of multiple-units in the form of coated delayed release multiple units for extended release of the NSAID substance, said units coated with a coating substantially water-insoluble, but water-diffusible and substantially pH-independent, wherein said second NSAID-containing fraction of multiple-units releases from about 6% to 30% of said NSAID substance within 0.5 hours upon dissolution testing by dissolution method III, and wherein the release of said second NSAID-containing fraction is independent of the release of said first NSAID-containing fraction.

2. The composition according to claim 1, wherein the first fraction when subjected to dissolution method II, about 70% w/w of the total amount of NSAID substance present in the first fraction is released within the first 20 min of the test.

3. The composition according to claim 1, wherein the quick release and the extended release are adapted such that the first fraction is substantially released in vitro when the in vitro release from the second fraction is initiated corresponding to at least 50% w/w release of the NSAID substance contained in the first fraction at the time when at the most 15% w/w of the NSAID substance contained in the second fraction is released as determined by dissolution method III.

4. The composition according to claim 1, wherein the first NSAID-containing fraction is in the form of uncoated units and NSAID substance contained in the first fraction has a $pK_a$ value between from about 3.0 to 5.5.

5. The composition according to claim 1, wherein the first NSAID-containing fraction is in the form of uncoated units and the NSAID substance has a solubility in 0.1 N hydrochloric acid at room temperature of at the most about 0.5% w/v.

6. The composition according to claim 1, wherein the first NSAID-containing fraction is present in the form of coated units and the NSAID substance contained in the first fraction has a $pK_a$ value of at least 5.0.

7. The composition according to claim 1, wherein the first NSAID-containing fraction is present in the form of coated units and the NSAID substance has a solubility in 0.1 N hydrochloric acid at room temperature of at least about 0.1% w/v.

8. The composition according to claim 1 for the administration of a therapeutically and/or prophylactically effective amount of an NSAID substance to obtain both a relatively fast onset of the therapeutic effect and the maintenance of therapeutically active plasma concentration for a relatively long period of time, a unit dosage of the composition comprising at least two fractions as follows:
   a first fraction of quick release multiple-units for relatively quick release in vivo of an NSAID substance to obtain a therapeutically and/or prophylactically active plasma concentration within a relatively short period of time, and
   a second fraction of coated modified release multiple-units for extended release in vivo of an NSAID substance to maintain a therapeutically and/or prophylactically active plasma concentration in order to enable dosing once or twice daily,
   the formulation of the first and the second fractions, with respect to release therefrom and with respect to the ratio between the first and the second fraction in the unit dosage, being adapted so as to obtain:
      a relative quick in vitro release of the NSAID substance from the first fraction of quick release multiple-units, as determined by dissolution method II,
      an extended in vitro release of the NSAID substance from the second fraction of extended release multiple-units relative to the in vitro release of the first fraction of the NSAID substance, as determined by dissolution method III,
      the quick release and the extended in vitro release being adapted so that the first fraction is substantially released when the release from the second fraction is initiated corresponding to at least 50% w/w release of the NSAID substance contained in the first fraction at the time when at least about 15% w/w of the NSAID substance contained in the second fraction is released as determined by dissolution method III.

9. The composition according to claim 1, wherein the NSAID substance is selected from the group consisting of lornoxicam, diclofenac, nimesulide, ibuprofen, piroxicam, piroxicam complexed with betacyclodextrin, naproxen, ketoprofen, tenoxicam, aceclofenac, indometacin, nabumetone, acemetacin, momiflumate, meloxicam, flurbiprofen, tiaprofenic-acid, proglumetacin, mefenamic acid, fenbufen, etodolac, tolfenamic acid, sulindac, phenylbutazone, fenoprofen, tolmetin, acetylsalicylic acid, dexibuprofen, and pharmaceutically acceptable salts, complexes and/or prodrugs thereof and mixtures thereof.

10. The composition according to claim 1, wherein the NSAID substance in the first fraction is the same as the NSAID substance contained in the second fraction.

11. The composition according to claim 1, wherein the NSAID substance in the first fraction is different from the NSAID substance contained in the second fraction.

12. The composition according to claim 1, wherein the NSAID substance in the first fraction is lornoxicam.

13. The composition according to claim 1, wherein the NSAID substance in the second fraction is lornoxicam.

14. The composition according to claim 1, comprising a further active drug substance.

15. The composition according to claim 1, wherein a further active drug substance is included in at least one of the first and second fraction.

16. The composition according to claim 14, wherein the further active drug substance is selected from the group consisting of an antidepressant, an opioid, a prostaglandine analog, a glucocorticosteroid, a cytostaticum, a $H_2$ receptor antagonist, a proton pump inhibitor and an antacidum.

17. The composition according to claim 14, wherein the further active drug substance is selected from the group consisting of paracetamol, penicillamine, sulfasalazine and auranorfin.

18. The composition according to claim 1, wherein the NSAID substance is lornoxicam.

19. The composition according to claim 1, wherein the quick release multiple-units of the first fraction have a mean particle size of at the most about 250 µm.

20. The composition according to claim 1, wherein the in vitro dissolution characteristics of the first fraction of quick release multiple-units provides within 1 hour a release of the NSAID substance of at least 50% w/w as determined by dissolution method II.

21. The composition according to claim 1, wherein the in vitro dissolution characteristics of the second fraction of extended release multiple-units provides within 1 hour a release of the NSAID substance in the range of 0%–30% w/w as determined by dissolution method III.

22. The composition according to claim 1, wherein the in vitro dissolution characteristics of the second fraction of extended release multiple-units provides within 3 hours a release of the NSAID substance in the range of about 10%–70% w/w as determined by dissolution method III 23. The composition according to claim 1, wherein the in vitro dissolution characteristics of the second fraction of extended release multiple-units provides within 6 hours a release of the NSAID substance in the range of about 35%–95% w/w as determined by dissolution method III.

24. The composition according to claim 1, wherein the in vitro dissolution characteristics of the second fraction of modified release multiple-units provides within 9 hours a release of the NSAID substance in the range of about 50%–100% w/w as determined by dissolution method III.

25. The composition according to claim 1, wherein the in vitro dissolution characteristics of the first and second fractions are adapted such that the NSAID substance of the first fraction is substantially released at the time when the release of the NSAID substance from the second fraction is initiated, corresponding to at least 50% w/w release of NSAID substance from the first fraction at the time where at the most about 15% w/w of the NSAID substance in the second fraction is released as determined by dissolution method III.

26. The composition according to claim 1, wherein the in vitro dissolution characteristics of the first and second fractions are adapted such that the NSAID substance of the first fraction is substantially released at the time where the release of the NSAID substance from the second fraction is initiated, corresponding to at least 70% w/w release of NSAID substance from the first fraction at the time where at the most about 20% w/w of the NSAID substance in the second fraction is released-as determined by dissolution method III.

27. The composition according to claim 1, wherein the in vitro dissolution characteristics of the composition provides within 1 hour a release of the NSAID substance from the composition in the range of about 5–50% w/w as determined by dissolution method m.

28. The composition according to claim 1, wherein the in vitro dissolution characteristics of the composition provides within 3 hours a release of the NSAID substance in the range of about 20–80% w/w as determined by dissolution method III.

29. The composition according to claim 1, wherein the in vitro dissolution characteristics of the composition provides within 6 hours a release of the NSAID substance in the range of about 40–98% w/w as determined by dissolution method III.

30. The composition according to claim 1, wherein the in vitro dissolution characteristics of the composition provides within 9 hours a release of the NSAID substance in the range of about 50–100% w/w as determined by dissolution method III.

31. The composition according to claim 1, wherein the percentage of NSAID substance in the first fraction is in the range of about 5%–50% w/w relative to the total amount of NSAID substance in the composition.

32. The composition according to claim 1, wherein the percentage of NSAID substance in the second fraction is in the range of about 30%–99% w/w relative to the total amount of NSAID substance in the composition.

33. The composition according to claim 1, wherein the multiple-units of the second fraction are coated cross-sectionally substantially homogeneous pellets.

34. The composition according to claim 1, wherein the multiple-units of the first fraction are cross-sectionally substantially homogeneous pellets.

35. The composition according to claim 1, wherein the first fraction is coated units and the coating is a substantially water-insoluble, but water-diffusible and substantially pH-independent coating.

36. The composition according to claim 1, wherein a unit dosage of the composition comprises from about 1 to about 32 mg of the NSAID substance.

37. The composition according to claim 1, wherein a unit dosage comprises from about 1 mg to about 1.6 g from about 1 mg to about 1.2 g of the NSAID substance.

38. The composition according to claim 1, wherein a unit dosage comprises from about 50 mg to about 1.1 g of the NSAID substance.

39. The composition according to claim 1, wherein a unit dosage comprises from about 100 mg to about 1.0 g of the NSAID substance.

40. The composition according to claim 1, wherein a unit dosage comprises from about 200 mg to about 900 mg of the NSAID substance.

41. The composition according to claim 1, wherein a unit dosage comprises from about 300 mg to about 800 mg of the NSAID substance.

42. The composition according to claim 1, wherein the unit dosage of the composition is in the form of a capsule, tablet or sachet.

43. The composition according to claim 1, wherein the NSAID substance is lomoxicam and the unit-dosage of the composition contains 4, 8, 12, 16, 20, 24, 28, 32 or 36 mg of lomoxicam.

44. A process for the preparation of a unit dosage form of an oral pharmaceutical modified release composition comprising the steps of:

i) providing a first fraction of quick release multiple-units for relatively quick release in vivo of an NSAID substance, wherein said fraction comprises an antacid or an alkaline agent and wherein the quick in vitro release being such that when subjecting the first NSAID-containing fraction to dissolution method II employing 0.07 N HCl as dissolution medium at least 50% w/w of the NSAID substance is released within the first 20 min of the test;

ii) providing a second fraction of coated extended release multiple-units for extended release in vivo of an NSAID substance, wherein said coated-units comprise a coating substantially water-insoluble, but water-diffusible and substantially pH-independent;

iii) combining and formulating the first and the second fractions with respect to release therefrom and with respect to the ratio between the first and the second fraction such that the first fraction is substantially released when the in vitro release from the second fraction is initiated, corresponding to at least about 50% w/w release of the NSAID substance from in the first fraction at the time when at the most about 15% w/w of the NSAID substance in the second fraction is released as determined by dissolution method III as defined herein; and iv) incorporating into the unit dosage form at least said two fractions i) and ii).

45. A method for treating a patient suffering from pain and/or inflammatory conditions comprising administering to the patient an effective amount of an NSAID substance in the form of a composition as defined in any one of claims 1–43 once or twice daily.

46. A method for administering a therapeutically and/or prophylactically effective amount of an NSAID substance to a patient in need thereof to obtain both a relatively fast onset of the therapeutic effect and the maintenance of therapeutically active plasma concentration for a relatively long period of time, the method comprising administering once or twice daily a unit dosage of a composition comprising at least two fractions as follows:

a first fraction of quick release multiple-units for relatively quick release in vivo of an NSAID substance to obtain a therapeutically and/or prophylactically active plasma concentration within a relatively short period of time, wherein said fraction comprises an antacid or an alkaline agent and wherein the quick in vitro release is such that, when subjecting the first NSAID-containing fraction to dissolution method II employing 0.07 N HCl as dissolution medium, at least 50% w/w of the NSAID substance is released within the first 20 min of the test; and a second fraction of coated modified release multiple-units for extended release in vivo of an NSAID substance to maintain a therapeutically and/or prophylactically active plasma concentration, wherein each of the multiple-units is coated with a coating substantially water-insoluble, but water-diffusible, and substantially pH-independent, wherein said second NSAID-containing fraction of multiple-units releases from about 6% to 30% of said NSAID substance within 0.5 hours upon dissolution testing by dissolution method III, and wherein the release of said second NSAID-containing fraction is independent of the release of said first NSAID-containing fraction.

47. The composition according to claim 1, wherein the second fraction is permeable in aqueous solution.

48. The composition according to claim 1, comprising at least 100 multiple units.

49. The composition according to claim 1, wherein the first fraction of multiple units is in granulate form.

50. The process according to claim 44, wherein the composition is as defined in any one of claims 1–43 and 47.

51. The method according to claim 46, wherein said composition is as defined in any one of claims 1–43 and 47.

* * * * *